US012697356B2

(12) United States Patent
Pelzer et al.

(10) Patent No.: US 12,697,356 B2
(45) Date of Patent: Aug. 4, 2026

(54) *BACILLUS SUBTILIS* STRAIN WITH PROBIOTIC ACTIVITY

(71) Applicant: EVONIK OPERATIONS GMBH, Essen (DE)

(72) Inventors: Stefan Pelzer, Gütersloh (DE); Daniel Petri, Vienna (AT); Christos Giatsis, Münster (DE); Stella Molck, Bielefeld (DE); Maike Kipker, Cologne (DE); Jessica Kleinbölting, Bielefeld (DE); Lorena Stannek-Göbel, Hannover (DE); Kiran Doranalli, Frankfurt (DE); John Khun Kyaw Htoo, Alzenau (DE); Claudia Borgmeier, Bensheim (DE); Sandra Herbold, Mannheim (DE); Guido Meurer, Seeheim-Jugenheim (DE)

(73) Assignee: Evonik Operations GmbH, Essen (DE)

( * ) Notice: Subject to any disclaimer, the term of this patent is extended or adjusted under 35 U.S.C. 154(b) by 654 days.

(21) Appl. No.: 16/627,195

(22) PCT Filed: Jun. 28, 2018

(86) PCT No.: PCT/EP2018/067422
§ 371 (c)(1),
(2) Date: Dec. 27, 2019

(87) PCT Pub. No.: WO2019/002471
PCT Pub. Date: Jan. 3, 2019

(65) Prior Publication Data
US 2020/0113952 A1      Apr. 16, 2020

(30) Foreign Application Priority Data

Jun. 30, 2017      (EP) ...................................... 17179052
Jul. 26, 2017      (CN) .......................... 201710618158.9

(51) Int. Cl.
| | |
|---|---|
| *A61K 35/742* | (2015.01) |
| *A23C 9/12* | (2006.01) |
| *A23C 9/152* | (2006.01) |
| *A23C 19/032* | (2006.01) |
| *A23C 19/06* | (2006.01) |
| *A23K 10/18* | (2016.01) |
| *A23K 50/30* | (2016.01) |
| *A23K 50/75* | (2016.01) |
| *A61P 1/14* | (2006.01) |
| *C12N 1/20* | (2006.01) |
| *C12N 1/205* | (2026.01) |
| *A61K 35/00* | (2006.01) |
| *C12R 1/125* | (2006.01) |

(52) U.S. Cl.
CPC .......... *A61K 35/742* (2013.01); *A23C 9/1203* (2013.01); *A23C 9/152* (2013.01); *A23C 19/032* (2013.01); *A23C 19/061* (2013.01);

*A23K 10/18* (2016.05); *A23K 50/30* (2016.05); *A23K 50/75* (2016.05); *A61P 1/14* (2018.01); *C12N 1/20* (2013.01); *C12N 1/205* (2021.05); *A61K 2035/115* (2013.01); *C12R 2001/125* (2021.05)

(58) Field of Classification Search
None
See application file for complete search history.

(56) References Cited

U.S. PATENT DOCUMENTS

| | | | |
|---|---|---|---|
| 4,919,936 A | 4/1990 | Iwanami et al. | |
| 5,227,294 A | 7/1993 | Carrera et al. | |
| 6,060,050 A | 5/2000 | Brown et al. | |
| 6,060,051 A | 5/2000 | Heins et al. | |
| 6,194,193 B1 | 2/2001 | Drahos et al. | |
| 6,849,256 B1 | 2/2005 | Farmer | |
| 7,247,299 B2 | 7/2007 | Lin et al. | |
| 7,981,659 B2 | 7/2011 | Kadoya et al. | |
| 9,247,757 B2 | 2/2016 | Schmidt et al. | |
| 9,622,484 B2 | 4/2017 | Taghavi et al. | |
| 9,844,573 B2 | 12/2017 | Nielsen et al. | |
| 10,138,444 B2 | 11/2018 | Ayangbile et al. | |
| 10,702,560 B2 | 7/2020 | Nielsen et al. | |
| 10,736,925 B2 | 8/2020 | Khuong Huu et al. | |
| 11,173,184 B2 | 11/2021 | Petri et al. | |
| 11,931,385 B2 | 3/2024 | Isaksen et al. | |
| 2008/0057047 A1 | 3/2008 | Sas et al. | |
| 2012/0328571 A1* | 12/2012 | Schmidt .................... | A61P 1/04 424/93.2 |
| 2014/0010792 A1 | 1/2014 | Rehberger et al. | |
| 2014/0065672 A1 | 3/2014 | Brune et al. | |

(Continued)

FOREIGN PATENT DOCUMENTS

| | | |
|---|---|---|
| CN | 105 969 708 | 9/2016 |
| CN | 106906169 | 6/2017 |

(Continued)

OTHER PUBLICATIONS

Li et al., "Bacillus subtilis RZ001 improves intestinal integrity and alleviates colitis by inhibiting the Notch signalling pathway and activating ATOH-1", Pathogens and Disease 2020, vol. 78, pp. 1-13 (Year: 2020).*

(Continued)

*Primary Examiner* — Michelle F. Paguio Frising

(74) *Attorney, Agent, or Firm* — Law Office of Michael A. Sanzo, LLC

(57) ABSTRACT

The current invention concerns a new *B. subtilis* strain with strong inhibition of swine and poultry related pathogens and its use as probiotic.

15 Claims, No Drawings
Specification includes a Sequence Listing.

(56) References Cited

U.S. PATENT DOCUMENTS

| | | |
|---|---|---|
| 2014/0342437 A1 | 11/2014 | Carpenter et al. |
| 2016/0326034 A1 | 11/2016 | Showell et al. |
| 2017/0073620 A1 | 3/2017 | Ayangbile et al. |
| 2017/0340683 A1 | 11/2017 | Petri et al. |
| 2021/0163357 A1 | 6/2021 | Müeller et al. |
| 2021/0228653 A1 | 7/2021 | Petri et al. |
| 2021/0392935 A1 | 12/2021 | Speckmann et al. |
| 2022/0088091 A1 | 3/2022 | Ochrombel et al. |
| 2022/0117264 A1 | 4/2022 | Giatsis et al. |
| 2022/0168363 A1 | 6/2022 | Stannek-Göebel et al. |
| 2022/0217998 A1 | 7/2022 | Riesen et al. |
| 2022/0241176 A1 | 8/2022 | Dieck et al. |
| 2023/0059825 A1 | 2/2023 | Giatsis et al. |
| 2023/0128187 A1 | 4/2023 | Speckmann et al. |

FOREIGN PATENT DOCUMENTS

| | | | | | |
|---|---|---|---|---|---|
| EP | 0 287 699 | 10/1988 | | | |
| EP | 1 010 754 | 6/2000 | | | |
| EP | 1 576 120 | 8/2009 | | | |
| JP | 2000-135096 | 5/2000 | | | |
| JP | 2003-190993 | 7/2003 | | | |
| JP | 2015-513910 | 5/2015 | | | |
| KR | 20080051798 | 6/2008 | | | |
| KR | 101467250 | 12/2014 | | | |
| WO | WO 98/28408 | 7/1998 | | | |
| WO | WO 00/43503 | 7/2000 | | | |
| WO | WO 03/066847 | 8/2003 | | | |
| WO | WO 2013/151361 | 10/2013 | | | |
| WO | WO 2016/108974 | 7/2016 | | | |
| WO | WO 2017/048636 | 3/2017 | | | |
| WO | WO-2017044953 A1 * | 3/2017 | ............ | A01N 63/00 | |
| WO | WO 2017/136944 | 8/2017 | | | |
| WO | WO 2017/207371 | 12/2017 | | | |
| WO | WO 2017/207372 | 12/2017 | | | |
| WO | WO 2018/045004 | 3/2018 | | | |
| WO | WO 2019/002471 | 1/2019 | | | |
| WO | WO 2019/002476 | 1/2019 | | | |
| WO | WO 2019/038153 | 2/2019 | | | |
| WO | WO 2019/063669 | 4/2019 | | | |
| WO | WO 2022/184637 | 9/2022 | | | |
| WO | WO 2022/184643 | 9/2022 | | | |
| WO | WO 2023/066533 A1 | 4/2023 | | | |

OTHER PUBLICATIONS

Irfan et al., "Optimization of process parameters for xylanase production by *Bacillus* sp. in submerged fermentation", Journal of Radiation Research and Applied Sciences, vol. 9, pp. 139-147 (Year: 2016).*

"Feed"; Encyclopædia Britannica. https://www.britannica.com/topic/feed-agriculture (accessed on Mar. 3, 2024) (Year: 2024).*

Allos, "*Campylobacter jejuni* Infections: Update on Emerging Issues and Trends," *Clinical Infectious Diseases* 32:1201-1206 (Apr. 2001).

Chatterjee, et al., "*Vibrio* Related Diseases in Aquaculture and Development of Rapid and Accurate Identification Methods," *J Marine Sci Res* Dev (2012); http://dx.doi.org/10.4172/2155-9910. S1-002.

Colles, et al., "Dynamics of *Campylobacter* colonization of a natural host, *Sturnus vulgaris* (European Starling)," *Environmental Microbiology* 11(1):258-267 (Jan. 2009).

Farzanfar, et al., "The use of probiotics in shrimp aquaculture," *FEMS Immunol. Med. Microbiol.* 48(2):149-158 (Nov. 2006).

Huang, et al., "Characterization of novel *Bacillus* strain N31 from mariculture water capable of halophilic heterotrophic nitrification-aerobic denitrification," *Journal of Bioscience and Bioengineering* 124(5):564-571 (Nov. 2017).

Mishra, et al., "Current Challenges of *Streptococcus* Infection and Effective Molecular, Cellular, and Environmental Control Methods in Aquaculture," *Mol. Cells* 41(6):495-505 (Jun. 2018).

Pulkkinen, et al., "Intensive fish farming and the evolution of pathogen virulence: the case of columnaris disease in Finland," *Proc. R. Soc. B.* 277:597-600 (Oct. 2009).

Vaseeharan, et al., "Control of pathogenic *Vibrio* spp. By *Bacillus subtillis* BT23, a possible probiotic treatment for black tiger shrimp *Penaeus monodon*," Letters in Applied Microbiology 36(2):83-87 (Jan. 2003).

U.S. Appl. No. 17/421,917, filed Jul. 9, 2021, US-2022/0117264 A1, Apr. 21, 2022, Giatsis.

U.S. Appl. No. 17/792,582, filed Jul. 13, 2022, Giatsis.

International Search Report for PCT/EP2017/062497 filed May 24, 2017 corresponding to copending U.S. Appl. No. 15/607,534.

Written Opinion of the International Searching Authority for PCT/EP2017/062497 filed May 24, 2017 corresponding to copending U.S. Appl. No. 15/607,534.

International Preliminary Report on Patentability for PCT/EP2017/062497 filed May 24, 2017 corresponding to copending U.S. Appl. No. 15/607,534.

Non Final Office Action mailed May 18, 2020 for copending U.S. Appl. No. 15/607,534.

Hoang, et al., "Recombinant Bacillus subtilis Expressing the Clostridium perfringens Alpha Toxoid is a Candidate Orally Delivered Vaccine against Necrotic Enteritis," *Infection and Immunity* 76(11):5257-5265 (Nov. 2008).

Jayaraman, et al., "Bacillus subtilis PB6 improves intestinal health of broiler chickens challenged with Clostridium perfringens-induced necrotic enteritis," *Poultry Science* 92(2):370-374 (Feb. 2013).

Argenzio, R.A., Secretion of the Stomach and Accessory Glands, p. 405-418. In: Reece, W.O. (ed.), Duke's Physiology of Domestic Animals; Twelfth Edition, Chapter 25; Cornell University Press, Ithaca, New York, (2004).

Argenzio, R.A., Digestive and Absorptive Functions of the Intestines, p. 419-437. In: Reece, W.O. (ed.), Duke's Physiology of Domestic Animals; Twelfth Edition, Chapter 26; Cornell University Press, Ithaca, New York, (2004).

Chen, et al., "Structural and Functional Characterization of Three Polyketide Synthase Gene Clusters in *Bacillus amyloliquefaciens* FZB 42," *Journal of Bacteriology* 188(11):4024-4036 (Jun. 2006).

Cutting, et al., Genetic Analysis (Chapter 2) In: Harwood CR, Cutting S M editors. Molecular Biological Methods for *Bacillus*. Chichester, England: John Wiley & Sons, Ltd.; pp. 27-74 (1990).

Hossain, et al., "Effect of *Bacillus subtilis, Clostridium butyricum* and *Lactobacillus acidophilus* endospores on growth performance, nutrient digestibility, meat quality, relative organ weight, microbial shedding and excreta noxious gas emission in broilers," *Veterinarni Medicinia* 60(2):77-86 (Feb. 2015).

Knap et al., "*Bacillus licheniformis* Prevents Necrotic Enteritis in Broiler Chickens," *Avian Diseases* 54:931-935 (2010).

Lumpkins, et al., "Evaluation of Distillers Dried Grains with Solubles as a Feed Ingredient for Broilers," *Poultry Science* 83:1891-1896 (accepted for publication Jul. 2004).

M'Sadeq, et al., "Towards the control of necrotic enteritis in broiler chickens with in-feed antibiotics phasing-out worldwide,"*Animal Nutrition* 1:1-11 (Nov. 2015).

Ohno, et al., "Production of a Lipopeptide Antibiotic, Surfactin, by Recombinant *Bacillus subtillis* in solid State Fermentation," *Biotechnology & Bioengineering* 47(2):209-214 (Jul. 1995).

Reddy, et al., "Effective feather degradation and keratinase production by *Bacillus pumilus* GRK for its application as bio-detergent additive," *Bioresourse Technology* 243:254-263 (Jun. 2017).

Rushen, et al., "Animal Behavior and Well-Being Symposium: Farm animal welfare assurance: Science and application," *J. Anim. Sci.*89:1219-1228 (2011).

Savva, et al., "Molecular Architecture and Functional Analysis of NetB, a Pore-forming Toxin from *Clostridium perfringens*," *JBC* 288(5):3512-3522 (Feb. 2013).

Scholz, et al., "Plantazolicin, a Novel Microcin B17/Streptolysin S-Like Natural Product from *Bacillus amyloliquefaciens* FZB42," *Journal of Bacteriology* 193(1):215-224 (Jan. 2011).

Sel Vam, et al., "Effect of *Bacillus subtillis* PB6, a natural probiotic on colon mucosal inflammation and plasma cytokines levels in inflammatory bowel disease," *Indian Journal of Biochemistry & Biophysics* 46:79-85 (Feb. 2009).

(56)     References Cited

OTHER PUBLICATIONS

Timbermont, et al., "Necrotic enteritis in broilers: an updated review on the pathogensis," *Avian Pathology* 40(4):341-347 (Aug. 2011).

Trampel, et al., Avian Digestion, pp. 488-500. In: Reece, W.O. (ed), Duke's Physiology of Domestic Animals; Twelfth Edition, Chapter 29; Cornell University Press, Ithaca, New York, USA (2004).

Uzal, et al., "Towards an understanding of the role of *Clostridium perfringens* toxins in human and animal disease," *Future Microbiol.* 9(3):361-377 (2014).

Wang, et al., "Comparison of gyrB gene sequences, 16S rRNA gene sequences and DNA-DNA hybridization in the *Bacillus subtilis* group," *International Journal of Systematic and Evolutionary Microbiology* 57(8):1846-1850 (Aug. 2007).

Zhou, et al., "Effects of *Bacillus licheniforms* on the growth performance and expression of lipid metabolism-related genes in broiler chickens challenged with *Clostridium perfringens*-induced necrotic enteritis," *Lipids in Health and Disease* 15:48; pp. 1-10 (Jan. 2016).

Gao, et al., "Isolation of *Bacillus subtilis*: screening for aflatoxins $B_1$, $M_1$, and $G_1$ detoxification," Eur. Food Res. Technol. 232:957-962 (2011).

Nithya, et al., Evaluation of the probiotic characteristics of *Bacillus* species isolated from different food sources, *Ann. Microbiol.* 63:129-137 (2013).

Final Office Action for copending U.S. Appl. No. 15/607,534, mailed Nov. 19, 2020.

Request for Continued Examination for copending U.S. Appl. No. 15/607,534, filed Mar. 19, 2021.

Amendment & Response to Accompany RCE for copending U.S. Appl. No. 15/607,534, filed Mar. 19, 2021.

Bishnoi, et al., "Draft Genome Sequence of a Natural Root Isolate, *Bacillus subtilis* UD1022, a Potential Plant Growth-Promoting Biocontrol Agent," *Genome Announcements* 3(4):e00696-15 (Jul./Aug. 2015).

U.S. Appl. No. 17/250,341, filed Jan. 7, 2021, US-2021/0163357 A1, Jun. 3, 2021, Müeller.

U.S. Appl. No. 17/049,155, filed Oct. 20, 2020, US-2022/0088091 A1, Mar. 24, 2022, Ochrombel.

U.S. Appl. No. 17/296,465, filed May 24, 2021, US-2021/0392935 A1, Dec. 23, 2021, Speckmann.

U.S. Appl. No. 17/608,274, filed Nov. 2, 2021, US-2022/0217998 A1, Jul. 14, 2022, Riesen.

U.S. Appl. No. 17/429,905, filed Aug. 10, 2021, US-2022/0168363 A1, Jun. 2, 2022, Stannek-Göebel.

U.S. Appl. No. 17/625,955, filed Jan. 10, 2022, US-2022/0241176 A1, Aug. 4, 2022, Dieck.

International Search Report for PCT/EP2018/067422, filed Jun. 28, 2018; corresponding to U.S. Appl. No. 16/627,195.

Written Opinion of the International Searching Authority for PCT/EP2018/067422, filed Jun. 28, 2018; corresponding to U.S. Appl. No. 16/627,195.

International Preliminary Report on Patentability for PCT/EP2018/067422, filed Jun. 28, 2018; corresponding to U.S. Appl. No. 16/627,195.

International Search Report for PCT/EP2017/062495 filed May 24, 2017, corresponding to copending application U.S. Appl. No. 16/305,811.

Written Opinion of the International Searching Authority for PCT/EP2017/062495 filed May 24, 2017, corresponding to copending application U.S. Appl. No. 16/305,811.

International Preliminary Report on Patentability for PCT/EP2017/062495 filed May 24, 2017, corresponding to copending application U.S. Appl. No. 16/305,811.

European Search Report for European application EP 16 17 2164 dated Nov. 28, 2016 (corresponding to copending U.S. Appl. No. 15/607,534).

Restriction Requirement for copending U.S. Appl. No. 15/607,534, mailed Sep. 14, 2018.

Response to Restriction Requirement for copending U.S. Appl. No. 15/607,534, filed Nov. 20, 2018.

Office Action for copending U.S. Appl. No. 15/607,534, mailed Apr. 8, 2019.

Amendment and Response to Accompany RCE for copending U.S. Appl. No. 15/607,534, filed Feb. 10, 2020.

Bacillus subtilis 16S rDNA sequence; NCBI Reference Sequence: NR_112116.2; retrieved Feb. 8, 2020.

Bacillus subtilis groEL sequence; NCBI Reference Sequence: NR_000964.3; retrieved Feb. 8, 2020.

Bacillus subtilis gyrB sequence; NCBI Reference Sequence: NR_000964.3; retrieved Feb. 8, 2020.

Bacillus subtilis rpoB sequence; NCBI Reference Sequence: NR_000964.3; retrieved Feb. 8, 2020.

Bacillus subtilis yqfD sequence; GenBank: D84432.1; retrieved Feb. 8, 2020.

XP-002764349; Bacillus licheniforms strain BCRC 15413 a6S ribosomal RNA gene, partial sequence, last updated Aug. 14, 2007.

Allaart, et al., "Net B-producing and beta2-producing *Clostridium perfringens* associated with subclinical necrotic enteritis in laying hens in the Netherlands," *Avian Pathology* 41(6):541-546 (received May 2012).

Aluwong, et al., "Effect of Yeast Probiotic on Growth, Antioxidant Enzyme Activities and Malondialdehyde Concentration of Broiler Chickens," *Antioxidants* 2:326-339 (2013).

Beauchamp, et al., "Superoxide Dismutase: Improved Assays and an Assay Applicable to Acrylamide Gels," *Anal. Biochem.* 44:276-287 (1971).

Bradford, "A Rapid and Sensitive Method for the Quatitation of Microgram Quantities of Protein Utilizing the Principle of Protein-Dye Binding," *Anal. Biochem.* 72:248-254 (1976).

Collins, et al., "*Streptococcus gallinaceus* sp. nov., from chickens," *International Journal of Systematic and Evolutionary Microbiology* 52:1161-1164 (2002).

Den Besten, et al., "Phenotypic and Transcriptomic Analyses of Mildly and Severly Salt-Stressed *Bacillus cereus* ATCC 14579 Cells," *Applied and Environmental Microbiology* 75(12):4111-4119 (Jun. 2009).

Glaser, et al., "Identification and Isolation of a Gene Required for Nitrate Assimilation and Anaerobic Growth of *Bacillus subtilis*," *Journal of Bacteriology* 177(4):1112-1115 (Feb. 1995).

Goyette-Desjardins, et al., "*Streptococcus suis*, an important pig pathogen and emerging zoonotic agent—an update on the world-wide distribution based on serotyping and sequence typing," *Emerging Microbes and Infections* 3(6): e45 (published online Jun. 2014).

Kense, et al., "*Enterococcus cecorum* infections in broiler breeders and their offspring: molecular epidemiology," *Avian Pathology* 40(6):603-612 (2011).

Larsen, et al., "Characterization of *Bacillus* spp. strains for use as probiotic additives in pig feed," *Appl. Microbiol. Biotechnol.* 98(3):1105-1118 (Published online Nov. 2013).

Lin, et al., "Acute heat stress induces oxidative stress in broiler chickens," *Comparative Biochemistry and Physiology, Part A* 144:11-17 (2006).

Mishra, et al., "Probiotics as Potential Antioxidants: A Systematic Review," *J. Agric. Food Chem.* 63:3615-3626 (2015).

Oelschlaeger, "Mechanisms of probiotic action—A review," *International Journal of Medical Microbiology* 300:57-62 (2010).

Palop, et al., "Influence of pH on heat resistance of *Bacillus licheniformis* in buffer and homogenised foods," *International Journal of Food Microbiology* 29:1-10 (Feb. 1996).

Parente, et al., "A comparison of methods for the measurement of bacteriocin activity," *Journal of Microbiological Methods* 22:95-108 (Apr. 1995).

Songer, et al., "Clostridial enteric infections in pigs," *J. Vet. Diagn. Invest.* 17:528-536 (2005).

Songer, et al., "Infection of neonatal swine with *Clostridium difficile*," *Swine Health Prod.* 8(4):185-189 (2000).

Teo, et al., "Inhibition of *Clostridium perfringens* by a Novel Strain of Bacillus subtilis Isolated from the Gastrointestinal Tracts of Healthy Chickens," *Applied and Environmental Microbiology* 71(8):4185-4190 (Aug. 2005).

(56)　　　　　　References Cited

OTHER PUBLICATIONS

Woodbury, et al., "An Improved Procedure Using Ferricyanide for Detecting Catalase Isozymes," *Anal. Biochem.* 44:301-305 (1971).

U.S. Appl. No. 15/607,534, filed May 29, 2017, US-2017-0340683 A1, Nov. 30, 2017, Petri.

U.S. Appl. No. 16/305,811, filed Nov. 29, 2018, Petri.

Bampidis, et al., (EFSA Panel on Additives and Products or Substrates used in Animal Feed), "Safety and efficacy of *Bacillus subtilis* PB6 (*Bacilus velezensis* ATCC PTA-6737) as a feed additive for chickens for fattening, chickens reared for laying, minor poultry species (except for laying purposes), ornamental, sporting and game birds," *ESFA Journal* 18(11):6280 pp. 1-10 (adopted Sep. 2020).

Hong, et al., "The use of bacterial spore formers as probiotics," *FEMS Microbiology Reviews* 29:813-835 (published online Dec. 2004).

"Bacillus subtilis strain UD1022, complete genome," Feb. 28, 2016; retrieved from the internet Mar. 31, 2021; https://www.ncbi.nlm.nih.gov/nuccore/CP011534.1?report=fasta.

Notice of Allowance for copending U.S. Appl. No. 15/607,534, mailed Jul. 19, 2021.

Response to Non Final Office Action for copending U.S. Appl. No. 15/607,534, filed Sep. 16, 2020.

U.S. Appl. No. 17/788,239, filed Jun. 22, 2022, US-2023/0128187 A1, Apr. 27, 2023, Speckmann.

Lalloo, et al., "Isolation and selection of *Bacillus* spp. As potential biological agents for enhancement of water quality in culture of ornamental fish," *Journal of Applied Microbiology* 103:1471-1479 (2007).

Alignment KY244143.1 with instant Seq Id No. 1 (Year 2025).

Macwilliams, M. P et al. ASM "Luria Broth (LB) and Luria Agar (LA) Media and Their Uses Protocol," published in 2016, pp. 1-4, downloaded from https://asm.org/protocols/luria-broth-lb-and-agar-la-media-and-their-u (Year 2016).

Cho, et al., "In vitro degradation of zearaleone by Bacillus subtilis," published on Aug. 10, 2010, Biotechnol. Lett. Vol. 32, pp. 1921-1924 (Year 2010).

Crab, et al., "Bio-flocs technology application in over-wintering of tilapia," published in 2009,Aquaculture Engineering vol. 40, pp. 105-112. (year 2009).

Guisinger, et al., "Amino Acid Immobilization of Copper Surface Diffusion on Cu(111)," published Mar. 12, 2019, Adv. Mater. Interfaces, vol. 6, 1900021, pp. 1-8. (year 2019).

Liu, et al., "Dietary administration of Bacillus subtilis HAINUP40 enhances growth, digestive enzyme activities, inate immune responses and disease resistance of tilapia, Oreochromis niloticus," published on Dec. 2, 2016, Fish & Shellfish Immunology, vol. 60, pp. 326-333. (Year 2016).

MedlinePlus ("Bile", published on Jul. 15, 2017, downloaded from https://Aweb.archive.org/web/20170715220014/https:// medlineplus.gov/ency/article/002237.htm (Year 2017).

Nicholson, et al., "Exploring the Low-Pressure Growth Limit: Evolution of Bacillus subtilis in the Laboratory to Enhanced Growth at 5 Kilopascals," published on Oct. 1, 2010, Appl. Environ. Microbiol. Vol. 72, No. 22, pp. 7559-7565. (Year 2010).

Pirofsky, et al., "Q&A: What is a pathogen? A question that begs the point," published on Jan. 31, 2012, BMC Biology vol. 10, No. 6, pp. 1-3. (Year 2012).

Sakata, et al., "Factors affecting the germination of Bacillus subtilis spores," published in 1975, Mem. Fac. Fish., Kagoshima Univ., vol. 24, pp. 139-147. (Year 1975).

Schrein, "What is an animal?" published on Feb. 5, 2016, downloaded from https://www.sapiens.org/biology/what-is-an-animal/. (Year 2016).

Shifeng, et al., "*Bacillus* sp. (in: firmicutes) 16S ribosomal RNA gene, partial sequence," published on Dec. 4, 2016, NCBI, pp. 1-2. (Year 2016).

Xia, et al., "Isolation and characterization of a Bacillus subtilis strain with aflatoxin B1 biodegradation capability," published on Dec. 26, 2016, Food Control, vol. 75, pp. 92-98 (Year 2016).

Ye, et al., "Global Gene Expression Profiles of Bacillus subtilis Grown under Anaerobic Conditions," published in Aug. 2000, Journal of Bacteriology, vol. 182, No. 16, pp. 4458-4465. (Year 2000).

* cited by examiner

SEQUENCE LISTING

<160> NUMBER OF SEQ ID NOS: 5

<210> SEQ ID NO 1
<211> LENGTH: 1537
<212> TYPE: DNA

<213> ORGANISM: Bacillus subtilis

<400> SEQUENCE: 1

```
agagtttgat cctggctcag gacgaacgct ggcggcgtgc ctaatacatg caagtcgagc      60
ggacagatgg gagcttgctc cctgatgtta gcggcggacg ggtgagtaac acgtgggtaa     120
cctgcctgta agactgggat aactccggga aaccggggct aataccggat ggttgtttga     180
accgcatggt tcaaacataa aaggtggctt cggctaccac ttacagatgg acccgcggcg     240
cattagctag ttggtgaggt aacggctcac caaggcgacg atgcgtagcc gacctgagag     300
ggtgatcggc cacactggga ctgagacacg gcccagactc ctacgggagg cagcagtagg     360
gaatcttccg caatggacga aagtctgacg gagcaacgcc gcgtgagtga tgaaggtttt     420
cggatcgtaa agctctgttg ttagggaaga caagtaccg ttcgaatagg gcggtacctt      480
gacggtacct aaccagaaag ccacggctaa ctacgtgcca gcagccgcgg taatacgtag     540
gtggcaagcg ttgtccggaa ttattgggcg taaagggctc gcaggcggtt tcttaagtct     600
gatgtgaaag cccccggctc aaccggggag ggtcattgga aactgggaa cttgagtgca      660 gaagaggaga gtggaattcc acgtgtagcg gtgaaatgcg tagagatgtg gaggaacacc     720
agtggcgaag cgactctct ggtctgtaac tgacgctgag gagcgaaagc gtggggagcg      780
aacaggatta gataccctgg tagtccacgc cgtaaacgat gagtgctaag tgttaggggg     840
tttccgcccc ttagtgctgc agctaacgca ttaagcactc cgcctgggga gtacggtcgc     900
aagactgaaa ctcaaaggaa ttgacggggg cccgcacaag cggtggagca tgtggtttaa     960
ttcgaagcaa cgcgaagaac cttaccaggt cttgacatcc tctgacaatc ctagagatag    1020
gacgtcccct tcggggcag agtgacaggt ggtgcatggt tgtcgtcagc tcgtgtcgtg     1080
agatgttggg ttaagtcccg caacgagcgc aaccccttgat cttagttgcc agcattcagt    1140
tgggcactct aaggtgactg ccggtgacaa accggaggaa ggtggggatg acgtcaaatc    1200
atcatgcccc ttatgacctg gctacacac gtgctacaat ggacagaaca aagggcagcg     1260
aaaccgcgag gttaagccaa tcccacaaat ctgttctcag ttcggatcgc agtctgcaac    1320
tcgactgcgt gaagctggaa tcgctagtaa tcgcggatca gcatgccgcg gtgaatacgt    1380
tcccgggcct tgtacacacc gcccgtcaca ccacgagagt ttgtaacacc gaagtcggt     1440 gaggtaacct tttaggagcc agccgccgaa ggtgggacag atgattgggg tgaagtcgta    1500
acaaggtagc cgtatcggaa ggtgcggctg gatcacc                             1537
```

<210> SEQ ID NO 2
<211> LENGTH: 1197
<212> TYPE: DNA
<213> ORGANISM: Bacillus subtilis

<400> SEQUENCE: 2

```
gtgaaaaata aatggctgtc tttttttcg ggtaaggtcc agcttgaatt gacgggaaga      60
gggattgagc ggctccttaa tgaatgcaca agacagggga ttccggtctt tcatgtcaaa     120
aaaaagaaag aagccgtatc gttatatata cagcttcagg atgtacatgc ctttcggcgg     180
gtgagaagta aatttaaatg taaagcccga tttatcaatc ggaagggatt tcccttcctg     240
ttgctgaaat caaagctgaa tataggattt acgatcggtt ttgcgatttt tttcatcctt     300
ttgtttttac tttccaatat ggtgtggaaa attgatgtga caggcgctaa gcctgaaaca     360
gaacatcaaa tgaggcagca tcttaatgaa atcggcgtca aaaagggccg tctgcagttt     420
ttaatgatgt cgcccgaaaa aatacagaaa tcgttaacca atggaataga caatatcact     480
```

```
tgggtcggag ttgatctgaa ggggacgacc attcacatga aagttgtgga gaaaaatgaa       540
cccgaaaaag aaaagtatgt tagcccgcgc aatattgtcg ccaaaaagaa agcaaccatt       600
acgagaatgt ttgtgcaaaa aggacagcct atggccgcca tacacgatca tgttgaaaag       660
gggcagctgc ttgtttcggg actgatcggc agcgaagacc atcagcagga agttgcctca       720
aaagcagaaa tttacggaga aacctggtat agatcagaag tgacagtccc gcttgaaaca       780
ttatttaacg tctatacggg caaagtaagg acaaagcaca agctttctat tggttctttg       840
gcaatcccga tctgggggat gacgtttaaa aaagaggaat tgaagcatcc aaaaacagaa       900
aaagaaaagc attcgcttca tttttctcgga tttaagctcc ctgtatctta tgtcaaagag       960
caaacgagag aaagtgaaga ggctttgcga aaatatacga agaagaagc agttcaagaa      1020 ggcattaaat tgggtaaaca ggatgtagag gataaaatag gcgaaaacgg cgaggtgaaa      1080
agtgaaaaag ttttgcacca gactgttgag aatggtaaag taaagttgat tattctctac      1140
caagttatag aagatatcgt tcaaaccaca cctattgtca gggagactga agaatga        1197
```

```
<210> SEQ ID NO 3
<211> LENGTH: 1923
<212> TYPE: DNA
<213> ORGANISM: Bacillus subtilis

<400> SEQUENCE: 3
gtggctatgg aacagcagca aaacagttat gatgaaaatc agatacaggt actagaagga        60
ttggaagctg ttcgtaaaag accggggatg tatatcggtt cgacaaacag caaaggcctt       120
caccacctgg tatgggaaat tgtcgacaat agtattgacg aagccctcgc cggttattgt       180
acggatatca atatccaaat cgaaaaagac aacagtatca cggttgtaga taatggccgc       240
ggtattccag tcggtattca tgaaaaaatg ggccgtcctg cggtagaagt cattatgacg       300
gtgcttcatg caggaggaaa atttgacgga agcggctata aagtatccgg aggattacac       360
ggtgtaggtg cgtcggtcgt aaacgcacta tcaacagagc ttgatgtgac ggttcaccgt       420
gacggtaaaa ttcaccgcca aacctataaa cgcggagttc cggttacaga ccttgaaatc       480
attggcgaaa cggatcatac aggaacgacg acacattttg ttccggaccc tgaaattttc       540
acagaaacaa ccgagtatga ttatgatctg cttgcaaacc gcgtgcgtga attagccttt       600
ttaacaaagg gcgtaaacat cacgattgag gataaacgtg aaggacaaga gcgcaaaaat       660
gaataccatt acgaaggcgg aattaaaagt tatgtagagt atttaaaccg ttctaaagag       720
gttgtccatg aagagccgat ttacattgaa ggcgaaaagg acggcataac ggttgaagta       780
gctttgcaat acaatgacag ctacacaagc aacatttact cgtttacaaa caacattaac       840
acgtacgaag gcggtaccca tgaagctggc tttaaaacgg gcctgactcg tgttatcaac       900
gattacgcca gaaaaaaagg gcttattaaa gaaaatgatc caaacctaag cggagatgac       960
gtaagggaag ggctgacagc gattatttca atcaaacacc ctgatccgca gtttgagggc      1020
caaacgaaaa caaagctggg caactcagaa gcacggacga tcaccgatac gttattttct      1080
gcggcgatgg aaacatttat gctggaaaat ccagatgcgg ccaaaaaaat tgtcgataaa      1140
ggcttaatgg cagcaagagc aagaatggct gcgaaaaaag cgcgtgaact aacacgccgt      1200
aagagtgctt tggaaatttc aaacctgccc ggtaagttag cggactgctc ttcaaaagat      1260
ccgagcatct ccgagttata tatcgtagag ggtgactctg ccggaggatc tgctaaacaa      1320
ggacgcgaca gacatttcca agccattttg ccgcttagag gtaagatcct aaacgttgaa      1380
```

-continued

```
aaggccagac tggataaaat cctttctaac aacgaagttc gctctatgat cacagcgctc      1440
ggcacaggta tcggggaaga cttcaacctt gagaaagccc gttatcacaa agttgtcatt      1500
atgacagatg ccgatgttga cggcgcgcat atcagaacac tgctgttaac gttcttttac      1560
agatatatgc gccaaattat cgaaaatggc tacgtgtaca ttgcgcagcc gccgctctac      1620
aaggttcaac aggggaaacg cgttgaatat gcatacaatg acaaggagct tgaagagctg      1680
ttaaaaactc ttcctcaaac gcctaagcct ggactgcagc gttacaaagg tcttggtgaa      1740
atgaatgcca cccagctttg ggagacaacc atggatccta gctccagaac acttcttcag      1800
gtaactcttg aagatgcaat ggatgcggac gagacttttg aaatgcttat gggcgacaaa      1860
gtagaaccgc gccgaaactt catagaagcg aatgcgagat acgttaaaaa tcttgacatc      1920
taa                                                                   1923

<210> SEQ ID NO 4
<211> LENGTH: 3582
<212> TYPE: DNA
<213> ORGANISM: Bacillus subtilis

<400> SEQUENCE: 4
ttgacaggtc aactagttca gtatggacga caccgccagc gcagaagcta tgctcgcatt        60
agcgaagtgt tagaattacc aaatctcatt gaaattcaaa cctcttctta tcagtggttt       120
cttgatgagg gtcttagaga gatgtttcaa gacatatcac caattgagga tttcactggt       180
aacctctctc ttgagttcat tgattatagt ttaggtgagc ctaaatatcc tgtagaggaa       240
tcaaaagaac gtgatgtgac ttactcagct ccgctaagag tgaaggttcg tttaattaac       300
aaagaaactg gagaggtaaa agaccaagat gtcttcatgg gtgatttccc tattatgaca       360
gatacaggta cttttatcat taacggtgcg gaacgcgtta tcgtttccca gcttgttcgg       420
tctccaagtg tatatttcag tggtaaagta gacaaaaacg gtaaaaaagg ttttaccgca       480
actgtcattc caaccgtggc gcatggttta gaatacgaaa ctgatgcgaa agatgttgtt       540
tatgtccgca ttgatcgcac acgtaagttg ccggttacgg ttctttgcg tgctctcggc       600 ttcggctccg atcaagagat tcttgatctc ataggagaaa acgaatacct gcgaaatacg       660
cttgataaag ataacacaga aaacagcgac aaagcgttgc tggaaattta cgagcgtctc       720
cgtcctggag agccgcctac agtagaaaat gcgaaaagct tgcttgattc tcgtttcttt       780
gatccgaaac gatacgatct tgccaatgta ggacgctata aaattaataa aaaacttcat       840
attaagaatc gcctcttcaa tcagagactt gctgaaacgc ttgttgatcc tgaaacagga       900
gaaatccttg ctgaaaaagg tcagattctt gatagaagaa cacttgataa agtactgcca       960
tacttagaaa acggaatcgg tttcagaaag ctgtatccga atggcggcgt tgttgaagat      1020
gaagtaactc ttcaatcaat taaaatcttt gctccgactg atcaagaagg agaacaggtt      1080
attaatgtaa tcggcaatgc ttacatcgaa gaagagatta aaaacatcac gcctgctgat      1140
attatttctt caatcagcta cttcttcaac ctgctgcatg gagtaggaga cacagatgat      1200
atcgatcatc ttggaaaccg ccgtttacgt tctgtaggcg agcttcttca gaaccaattc      1260
cgtatcggtt taagccgtat ggagcgtgtg gttcgtgaga aatgtcaat tcaagatacg      1320 aatacaatta cgcctcagca gctgatcaat attcgtcctg ttattgcgtc cattaaagag      1380
ttctttggaa gctcacagct ttctcaattc atggatcaga cgaacccgct tgctgaatta      1440
acgcacaagc gccgtctgtc agcattagga ccgggcggat tgacacgtga gcgtgccgga      1500
atggaagtgc gtgacgttca ctactcccac tatggccgta tgtgtccgat tgaaacgcct      1560
```

-continued

```
gagggcccga acatcggttt gatcaactca ctttcatctt atgcaaaagt aaaccgtttt      1620
ggctttattg aaacgccata tcgccgcgtt gaccctgaaa cagggaaagt aacgggcaga      1680
atcgattact taactgctga tgaagaggat aactatgttg tcgctcaagc gaacgctcgt      1740
cttgatgacg aaggcgcctt tattgatgac agcatcgtag ctcgtttccg cggggagaac      1800
actgttgttt ccagaaatcg tgtagactac atggatgtat cgcctaagca ggttgtatct      1860
gctgcgacag catgtattcc gttcttagaa aacgatgact ccaaccgtgc cctcatggga      1920
gcgaacatgc agcgtcaggc tgtgcctttg atgcagccgg aagcgccatt cgttggaact      1980
ggtatggaat acgtatcagg aaaagactct ggtgccgctg ttatttgtaa acacccaggt      2040
atcgttgaac gcgtagaagc gaaaaacgtt tgggttcgcc gttatgaaga agtagacggc      2100
aaaaaagtaa aaggaaacct ggataaaatac agcctgctga aatttgtccg ctctaaccaa      2160
ggtacgtgct acaaccagcg tccgatcgta agtgtcggcg atgaagtggt aaaaggagaa      2220
atccttgctg acggtccttc tatggagctt ggtgaacttg cacttggccg taacgtaatg      2280
gtcggcttca tgacatggga tggctacaac tatgaggatg ccatcatcat gagtgaacgc      2340
ctagtgaagg atgatgttta tacatctatc cacattgaag aatacgaatc agaagcacgt      2400
gatacgaaac ttggacctga agaaatcact cgcgatattc caaacgtcgg tgaagatgca      2460
cttcgcaatc ttgatgaccg cggaatcatc cgtattgggg cagaagtaaa agacggagat      2520
cttcttgttg gtaaagtaac gcctaaaggc gtaactgaac tgactgcaga agaacgcctt      2580
cttcacgcca tctttggcga gaaagcccgc gaggttcgtg atacttctct tcgtgtgcct      2640
cacggcggcg gcggaattat ccatgacgtt aaagtcttca accgtgaaga cggagacgaa      2700
cttcctccag gtgttaacca gttagtacgc gtatatatcg ttcagaaacg taagatttct      2760
gaaggggata aaatggccgg tcgtcacggt aacaaaggtg ttatctctaa gattcttcct      2820
gaagaggata tgccttacct tcctgacggc acaccaattg atatcatgct taacccgctg      2880
ggcgtaccat cacgtatgaa catcgggcag gtattggaac ttcacatggg tatggccgct      2940
cgttaccttg gcattcacat cgcatctcct gtatttgacg gagcgcgaga agaggatgtc      3000
tgggaaacac ttgaagaagc cggcatgtct cgtgacgcca aaacagtgct ttacgacgga      3060
cgtactggcg agccgtttga taaccgtgta tctgtcggta tcatgtacat gatcaaactg      3120
gctcacatgg ttgacgataa acttcatgcg cgctctacag gcccttactc acttgttacg      3180
cagcagcctc ttggcggtaa agcgcaattt ggcggacagc gtttcggtga gatggaggtt      3240
tgggcacttg aagcttacgg tgcggcttac actcttcaag aaattctgac tgttaagtct      3300
gatgacgtgg ttggacgtgt gaaaacatac gaagccatcg ttaaaggcga caatgttcct      3360
gaaccaggtg ttccggaatc attcaaagta ttaatcaaag aacttcaaag cttaggtatg      3420
gatgtcaaaa tcctttctgg tgatgaagaa gaaatagaaa tgagagattt agaagacgaa      3480
gaagatgcga acaagctga cggcctggca ttatcaggtg atgaagagcc ggaagaaaca      3540
gcatctgcag acgttgaacg tgatgtagta acaaaagaat aa      3582
```

<210> SEQ ID NO 5
<211> LENGTH: 1632
<212> TYPE: DNA
<213> ORGANISM: Bacillus subtilis

<400> SEQUENCE: 5

```
atggcaaaag aaattaagtt tagtgaagaa gctcgccgcg caatgcttcg cggtgtcgat       60
```

-continued

```
gcacttgctg atgctgttaa agtaacttta ggaccaaaag gacgcaacgt ggttctagag      120
aaaaaattcg gttctccgtt aatcacaaat gacggtgtaa caatcgctaa agaaatcgag      180
cttgaagatg cgtttgaaaa catgggtgcg aagcttgttg ctgaagtagc cagcaaaaca      240
aacgacgttg ccggtgacgg tacaacaact gcgacagttc ttgcacaagc aatgatccgt      300
gaaggcctta aaaacgtaac agcaggcgct aaccctgtag gcgtgcgtaa aggtatggaa      360
caagctgtag ctgttgcaat cgaaaactta aaagaaattt ctaagccaat cgaaggcaaa      420
gagtctatcg ctcaggttgc tgcgatctct gctgctgatg aggaagtcgg aagccttatc      480
gctgaagcaa tggagcgcgt aggaaacgac ggcgttatca caatcgaaga gtctaaaggc      540
tttacaactg agcttgaagt tgttgaaggt atgcaattcg accgcggata tgcgtctcct      600
tacatggtaa ctgactctga taagatggaa gcggttcttg acaatcctta catcttaatc      660
acagacaaaa aaatcacaaa catccaagaa atccttcctg tgcttgagca ggttgttcag      720
caaggcaaac cattgcttct gatcgctgag gatgttgaag gcgaagcact tgcaacactt      780
gttgtgaaca aacttcgtgg cacattcaac gcagttgctg ttaaagctcc tggcttcggt      840
gaccgccgta aagcaatgct tgaagacatc gctgtcctta ctggcggaga agtcatcaca      900
gaagatcttg gccttgacct gaaatctact caaatcgctc aattgggacg cgcttctaaa      960
gttgtcgtta ctaaagaaaa cacaacaatc gttgaaggcg ctggcgaaac agacaaaatt     1020
tctgcccgcg tgactcaaat ccgcgctcaa gtggaagaaa caacttctga gttcgacaga     1080
gaaaaattac aagagcgtct tgcgaaactt gctggcggcg tagctgtcat taaagtcggc     1140
gctgcgactg aaactgagct gaaagagcgt aaacttcgca tcgaagacgc cctgaactca     1200
actcgcgcag ctgttgaaga aggcatcgta tccggtggtg gtacagcgct tgtaaacgta     1260
tataacaaag tcgctgcagt tgaagctgaa ggcgatgctc aaacaggtat caacatcgtg     1320
cttcgcgcgc ttgaagagcc aatccgtcaa atcgcacaca acgctggtct tgaaggatct     1380
gtcatcgttg agcgcctcaa aaacgaagaa atcggcgtag gcttcaacgc tgcaactggc     1440
gaatgggtaa acatgatcga aaaaggtatc gttgacccaa ctaaagttac acgctcagct     1500
cttcaaaacg ctgcgtctgt agctgcaatg ttcttaacaa ctgaagccgt tgtcgctgac     1560
aagccagaag aaaacgctgg cggcggaatg cctgatatgg gcggcatggg cggtatgggc     1620
ggcatgatgt aa                                                         1632
```

BACILLUS SUBTILIS STRAIN WITH PROBIOTIC ACTIVITY

CROSS REFERENCE TO RELATED APPLICATIONS

The present application is US national stage of international application PCT/EP2018/067422, which had an international filing date of Jun. 28, 2018, and which was published on Jan. 3, 2019. The PCT application claims priority to European application EP 17179052.0, filed on Jun. 30, 2017 and to Chinese application CN 201710618158.9, filed on Jul. 26, 2017. The contents of each priority application is hereby incorporated by reference herein in its entirety.

SEQUENCE LISTING

The instant application contains a Sequence Listing which has been submitted in ASCII format via EFS-Web. The Sequence Listing was created on Dec. 26, 2019, is named Pelzer-1 and is 13,437 bytes in size. This Sequence Listing is hereby incorporated by reference in its entirety.

The current invention concerns a new *B. subtilis* strain with strong inhibition of swine and poultry related pathogens and its use as probiotic.

The use of *B. subtilis* strains as probiotic ingredient in the feed industry has been disclosed before in the state of the art. The function of probiotics (also called "direct-fed microbials" or "DFM") is to influence the gut microflora in a positive way by supporting the growth of beneficial bacteria and/or the suppression of the growth of pathogenic bacteria. Ideally, by using probiotics the use of antibiotic growth promotors (AGPs) becomes redundant. But besides that, it is desirable that the probiotic fulfills further functions like helping in the digestion of specific feed ingredients.

Thus in view of the state of the art, there is a need for probiotics which influence the gut microflora in a positive way and beyond that desirably fulfill at least one further function.

Surprisingly it was found that the bacteria according to the current invention exhibit many advantageous features. Besides their ability to inhibit growth of *C. perfringens, C. difficile, S. aureus* subsp. *aureus, S. gallinaceus, S. suis, C. coli* and *E. cecorum*, the main commercially relevant pathogens of swine and poultry, they in particular show a very high proliferation rate in presence of bile and help to digest cellulose in a very effective way.

*Bacillus subtilis* DSM 32540 has been identified by targeted screening of naturally occurring isolates. It has been deposited with the DSMZ on Jun. 14, 2017 under the provisions of the Budapest Treaty on the International Recognition of the Deposit of Microorganisms for the Purpose of Patent Procedure under the Accession Number as mentioned before in the name of Evonik Degussa GmbH.

Thus a first subject of the current invention is a *Bacillus subtilis* strain and/or a preparation of said *Bacillus subtilis* strain selected from the following group:

a) The *Bacillus subtilis* strain as deposited under DSM 32540 at the DSMZ;

b) a mutant of the *Bacillus subtilis* strain as deposited under DSM 32540 having all identifying characteristics of the strain DSM 32540, wherein said mutant preferably has a DNA sequence identity to the strain DSM 32540 of at least 95%, preferably at least 96, 97 or 98%, more preferably at least 99 or 99.5% and/or wherein that mutant preferably has a genomic DNA sequence identity to the strain DSM 32540 of at least 95%, preferably at least 96, 97 or 98%, more preferably at least 99, 99.5 or 99.8%, in particular of 100%;

c) a preparation of (a) or (b);

d) a preparation containing an effective mixture of metabolites as contained in (a), (b) or (c).

The *Bacillus subtilis* strain as deposited under DSM 32540 at the DSMZ exhibits the following characterizing sequences:

a) a 16S rDNA sequence with a sequence identity of at least 99 or 99.5%, in particular 100%, to the polynucleotide sequence according to SEQ ID NO: 1;

b) a yqfD sequence with a sequence identity of at least 99 or 99.5%, in particular 100%, to the polynucleotide sequence according to SEQ ID NO: 2;

c) a gyrB sequence with a sequence identity of at least 99 or 99.5%, in particular 100%, to the polynucleotide sequence according to SEQ ID NO: 3;

d) an rpoB sequence with a sequence identity of at least 99 or 99.5%, in particular 100%, to the polynucleotide sequence according to SEQ ID NO: 4;

e) a groEL sequence with a sequence identity of at least 99 or 99.5%, in particular 100%, to the polynucleotide sequence according to SEQ ID NO: 5.

Thus, a further subject of the current invention is a *Bacillus subtilis* strain, in particular a *B. subtilis* strain with the characteristics as mentioned before, or a preparation thereof, wherein the *B. subtilis* strain exhibits at least one, preferably all, of the following characteristics:

a) a yqfD sequence with a sequence identity of at least 99.5%, more preferably at least 99.8 or 99.9%, above all 100%, to the polynucleotide sequence according to SEQ ID NO: 2;

b) a gyrB sequence with a sequence identity of at least 99.5%, more preferably at least 99.8 or 99.9%, above all 100%, to the polynucleotide sequence according to SEQ ID NO: 3;

c) an rpoB sequence with a sequence identity of at least 99.5%, more preferably at least 99.8 or 99.9%, above all 100%, to the polynucleotide sequence according to SEQ ID NO: 4;

d) a groEL sequence with a sequence identity of at least 99.5%, more preferably at least 99.8 or 99.9%, above all 100%, to the polynucleotide sequence according to SEQ ID NO: 5;

wherein the *B. subtilis* strain further preferably exhibits a 16S rDNA sequence with a sequence identity of at least 99%, more preferably at least 99.5, 99.8 or 99.9%, above all 100%, to the polynucleotide sequence according to SEQ ID NO: 1.

Thus, a further subject of the current invention is a *Bacillus subtilis* strain or a preparation thereof, in particular a *B. subtilis* strain with the characteristics as mentioned before, exhibiting two, three or four, preferably all, of the following characteristics:

a) a 16S rDNA sequence with a sequence identity of at least 99%, preferably at least 99.5%, more preferably at least 99.8 or 99.9%, above all 100%, to the polynucleotide sequence according to SEQ ID NO: 1;

b) a yqfD sequence with a sequence identity of at least 99%, preferably at least 99.5%, more preferably at least 99.8 or 99.9%, above all 100%, to the polynucleotide sequence according to SEQ ID NO: 2;

c) a gyrB sequence with a sequence identity of at least 99%, preferably at least 99.5%, more preferably at least 99.8 or 99.9%, above all 100%, to the polynucleotide sequence according to SEQ ID NO: 3;

d) an rpoB sequence with a sequence identity of at least 99%, preferably at least 99.5%, more preferably at least 99.8 or 99.9%, above all 100%, to the polynucleotide sequence according to SEQ ID NO: 4;

e) a groEL sequence with a sequence identity of at least 99%, preferably at least 99.5%, more preferably at least 99.8 or 99.9%, above all 100%, to the polynucleotide sequence according to SEQ ID NO: 5.

Thus, a particular subject of the current invention is also a *Bacillus subtilis* strain, exhibiting the following characteristics:

a) a 16S rDNA sequence according to SEQ ID NO: 1;

b) a yqfD sequence according to SEQ ID NO: 2;

c) a gyrB sequence according to SEQ ID NO: 3.

Preferably, this *B. subtilis* strain exhibits the following further characteristics:

d) an rpoB sequence according to SEQ ID NO: 4;

e) a groEL sequence according to SEQ ID NO: 5.

The strains of the current invention are preferably characterized by at least one, more preferably by all, of the following further features:

They are preferably able to grow under anaerobic conditions. Further, they are preferably able to degrade water-insoluble cellulose as well as protein under such anaerobic conditions.

Further, the strains of the current invention are preferably further able to degrade water-insoluble cellulose under aerobic conditions.

They preferably inhibit infectious bacteria very effectively, in particular at least one strain, preferably all strains, selected from *C. perfringens* ATCC 13124; *C. perfringens* BB-081 Cpe; *C. perfringens* BB 031 Cpe; *C. difficile* DSM 1296; *S. aureus* subsp. *aureus* DSM 20231; *S. gallinaceus* DSM 15349; *S. suis* DSM 9682, *C. coli* DSM 4689 and *E. cecorum* DSM 20683.

In particular they are preferably characterized by a pathogen clearance of at least 15 mm, more preferably at least 20 mm, in a well diffusion antagonism assay on LBKelly agar plates with respect to *C. perfringens* type strain ATCC 13124 and/or by a pathogen clearance of at least 20 mm with respect to *C. perfringens* strain BB-081_Cpe and/or a pathogen clearance of at least 15 mm, preferably at least 18 mm, with respect to *C. perfringens* strain BB_031_Cpe, respectively.

The strains according to the invention are preferably further characterized by being able to grow in the presence of 0.05 wt.-% acetic acid, 0.05 wt.-% propionic acid and/or 0.2 wt.-% lactic acid.

The strains according to the invention are preferably further characterized by exhibiting at least one, preferably all, of the following enzymatic activities: cellulase activity; xylanase activity; catalase activity; superoxide dismutase activity.

In particular, they are preferably characterized by a xylanase activity of at least 8 mU/mL, more preferably at least 10 mU/mL, in particular about 12 mU/mL.

The strains of the current invention preferably furthermore produce lactate and they are preferably further able to degrade mycotoxins.

The *B. subtilis* strains according to the invention are preferably further characterized by being able to grow in presence of 2 mM bile, more preferably in presence of 4 mM bile. In particular they are preferably characterized by being able to proliferate fast under such high bile concentrations.

In addition, the strains are preferably able to grow under high salt conditions, in particular in presence of 5 wt.-% of NaCl, more preferably in presence of 10 wt.-% NaCl, for at least one day.

Further the strains of the current invention preferably survive the high temperatures necessary for pelleting animal feed, in particular they preferably survive a temperature of 80° C., more preferably of 95 or 99° C., for at least 20 minutes.

Without wishing to be bound by any theory, it is thought that the *Bacillus subtilis* strains according to the current invention enhance animal health, in particular gut health, by a multifaceted mode of action, including the production of antibacterial metabolites with selective efficacy and the competition with pathogenic bacteria by better consuming the available nutrients, thereby suppressing effective establishment of pathogenic bacteria in the gut. Hereby the enzymes produced by *Bacillus subtilis* may help to establish a balanced gut microbiota by providing predigested nutrients.

It is a big advantage of probiotics in comparison to antibiotics, that they do not attack bacteria indiscriminately nor do they lead to antibiotic resistant strains of pathogenic bacteria. Normally they are able to selectively compete with pathogenic bacteria by production of antimicrobial substances with specific efficacy, and are ideally able to simultaneously enhance the growth and viability of beneficial gut microflora. Further, they are preferably able to stimulate a systemic immune response in the treated animals.

The mutant strains of DSM 32540 of the current invention are preferably spontaneous mutants. The term "spontaneous mutant" refers to mutants that arise from DSM 32540 without the intentional use of mutagens. Such spontaneous mutants may be obtained by classical methods, such as growing the *Bacillus subtilis* strain in the presence of UV light and/or by applying high temperature or protoplast formation and/or in the presence of a certain antibiotic to which the parent strain is susceptible and testing any resistant mutants for improved biological activity or improved ability to enhance one or more of the indicia of animal health, in particular gut health. Other methods for identifying spontaneous mutants are known to those of ordinary skill in the art. But besides these preferred spontaneous mutants all other kinds of mutants of DSM 32540, like mutants obtained by genetic engineering, are also comprised by the current invention.

One particular embodiment of the current invention are naturally non-occurring mutants, in particular spontaneous mutants as defined before, of the strain DSM 32540, characterized by the features as mentioned above.

In a preferred embodiment of the current invention, the strains and preparations of the present invention are preferably administered orally to animals or human beings.

Thus, a further subject of the current invention are compositions, such as feedstuffs, foodstuffs, drinking and rearing water as well as therapeutic compositions, containing a *B. subtilis* strain and/or a preparation of the current invention.

A further subject of the current invention is also the use of a *B. subtilis* strain and/or a preparation of the current invention as a probiotic ingredient (DFM) in feed or food products.

Preferred foodstuffs according to the invention are dairy products, in particular yoghurt, cheese, milk, butter and quark.

The cells of the strains of the current invention may be present, in particular in the compositions of the current invention, as spores (which are dormant), as vegetative cells (which are growing), as transition state cells (which are transitioning from growth phase to sporulation phase) or as a combination of at least two, in particular all of these types of cells. In a preferred embodiment, the composition of the current invention comprises mainly or only spores.

In addition or as alternative the cells of the strains may also be used in non-living, inactivated form, as also the non-living cells are expected to still have a probiotic effect. Ways to inactivate the cells are known to those skilled in the art.

The *Bacillus subtilis* strains of the current invention and compositions containing them, when administered to animals, preferably enhance the health of such animals and/or improve the general physical condition of such animals and/or improve the feed conversion rate of such animals and/or decrease the mortality rate of such animals and/or increase the survival rates of such animals and/or improve the weight gain of such animals and/or increase the productivity of such animals and/or increase the disease resistance of such animals and/or increase the immune response of such animals and/or establish or maintain a healthy gut microflora in such animals and/or reduce the pathogen shedding through the feces of such animals. In particular the strains and compositions of the current invention might be used to assist in re-establishing a healthy balance of the gut microflora after administration of antibiotics for therapeutic purposes.

A further subject of the current invention is therefore a method of enhancing the health of animals and/or of improving the general physical condition of animals and/or of improving the feed conversion rate of animals and/or of decreasing the mortality rate of animals and/or of increasing the survival rates of animals and/or of improving the weight gain of animals and/or of increasing the productivity of animals and/or of increasing the disease resistance of animals and/or of increasing the immune response of animals and/or of establishing or maintaining a healthy gut microflora in animals and/or of reducing the pathogen shedding through the feces of animals, wherein the strains and/or preparations of the current invention or the compositions of the current invention, which comprise such strain(s), are administered to animals.

A further subject of the current invention is therefore also the use of strains and/or preparations and/or compositions of the current invention for enhancing the health of animals and/or for improving the general physical condition of animals and/or for improving the feed conversion rate of animals and/or for decreasing the mortality rate of animals and/or for increasing the survival rates of animals and/or for improving the weight gain of animals and/or for increasing the productivity of animals and/or for increasing the disease resistance of animals and/or for increasing the immune response of animals and/or for establishing or maintaining a healthy gut microflora in animals and/or for reducing the pathogen shedding through the feces of animals, wherein the strains and/or preparations of the current invention or the compositions of the current invention, which comprise such strain(s), are administered to animals.

A further subject of the current invention are therefore also the strains and preparations of the current invention as mentioned before and the compositions of the current invention, containing those strains, for enhancing the health of animals and/or for improving the general physical condition of animals and/or for improving the feed conversion rate of animals and/or for decreasing the mortality rate of animals and/or for increasing the survival rate of animals and/or for improving the weight gain of animals and/or for increasing the productivity of animals and/or for increasing the disease resistance of animals and/or for increasing the immune response of animals and/or for establishing or maintaining a healthy gut microflora in animals and/or for reducing the pathogen shedding through the feces of animals.

"Increasing the productivity of animals" refers in particular to any of the following: production of more or higher quality eggs, milk or meat or increased production of weaned offspring.

The methods and uses of the strains, preparations and compositions of the current invention can be therapeutic or non-therapeutic. In a particularly preferred embodiment of the current invention, the methods and uses are non-pharmaceutic, in particular feeding applications.

As the untreated manure of animals due to pathogenic bacteria and other ingredients may have a detrimental environmental effect, in particular with respect to the animals themselves and/or with respect to human beings getting in contact with the manure, which can be avoided by either feeding the animals or directly treating the manure or the bedding of the animals with the strains, compositions or preparations of the current invention, therefore a further subject of the current invention is a method of controlling and/or avoiding detrimental environmental effects of manure or contaminated liquids, the method comprising the step of applying to manure, contaminated liquids, litter, a pit, or a manure pond at least one strain, one preparation and/or one composition according to the current invention. Preferably the composition is applied in liquid form, for example by spraying, or as a powder, for example by strewing.

As detrimental bacteria may have a negative influence on the consistency of litter and in particular may effect a rather fluid or highly fluid litter, which might lead to foot pad lesions of poultry and which can be avoided by feeding the animals with the strains, compositions or preparations of the current invention, therefore a further subject of the current invention is a method of controlling and/or improving the consistency of litter, in particular a method of ensuring a solid consistency of litter and/or a method of avoiding foot pad lesions, the method comprising the step of feeding animals, in particular poultry, with at least one strain, one preparation and/or one composition according to the current invention.

The strains and preparations according to the invention can also be used for improving the quality of water. A further subject of the current invention is therefore also a method of controlling and/or improving the quality of water or aqueous solutions, in particular of drinking water and/or rearing water, comprising the step of applying to water or an aqueous solution at least one strain and/or at least one preparation and/or at least one composition of the current invention.

Further, the strains and preparations according to the invention can also be used for treating microbial diseases of plants. A further subject of the current invention is therefore also a method of treating and/or preventing microbial diseases of plants, in particular of cultivated plants, comprising the step of applying to the plants at least one strain and/or at least one preparation and/or at least one composition of the current invention. The application may be carried out in liquid form, such as by spraying, or in solid form, in particular as a powder, preferably as a formulated powder.

By using the strains, preparations and compositions of the current invention preferably an improvement of at least one of the features as mentioned before is realized, wherein realization of the feature preferably means an improvement of at least 1%, more preferably of at least 3 or at least 5%, in comparison to an adequate negative control. As negative control averages known in the animal husbandry field may be used, but preferably as negative control animals which are subjected to the same treatment like the animals tested are used, but without administration of the strains and/or preparations of the current invention.

In particular, the strains, preparations and compositions of the current invention may be administered or fed to an animal in an amount effective to inhibit and/or decrease the growth of pathogenic bacteria in the animal gut. Such pathogenic bacteria include *Clostridia, Listeria, Salmonella, Enterococci, Staphylococci, Aeromonas, Streptococci, Campylobacter, Escherichia coli, Shigella, Haemophilus, Brachyspira* and *Vibrio*. Relatedly, the methods of the present invention may be used to decrease the amount of pathogenic bacteria, viruses and protozoans shed in animal feces. The methods of the present invention may also be used to maintain or increase the growth of beneficial bacteria, such as lactic acid bacteria, in the animal gut. By decreasing pathogenic bacteria and/or increasing or maintaining beneficial bacteria, the compositions of the present invention are able to maintain an overall healthy gut microflora.

Thus, a further subject of the current invention are also the strains, preparations and compositions of the current invention for inhibiting and/or decreasing the growth of pathogenic bacteria and/or for maintaining and/or increasing the growth of beneficial bacteria in an animal gut, wherein the pathogenic bacteria are preferably selected from *Clostridia*, in particular from *C. perfringens, C. difficile, C. novyi, C. septicum* and *C. colinum*, from *Listeria*, in particular from *L. monocytogenes, L. seeligeri* and *L. welshimeri*, from *Salmonella*, in particular *S. enterica* including the subspecies *enterica, arizonae, bongori* and in particular the serovars, *S. gallinarum, S. pullorum, S. typhimurium, S. enteritidis, S. cholerasuis, S. heidelberg* and *S. infantis*, from *Enterococci*, in particular *E. faecalis, E. faecium* and *E. cecorum*, from *Staphylococci*, in particular *S. aureus*, from *Aeromonas*, from Streptococci, in particular *S. suis* and *S. gallinaceus*, from *Campylobacter*, in particular *C. jejuni* and *C. coli*, from *Escherichia coli*, from *Haemophilus*, in particular *Haemophilus parasuis*, from *Brachyspira*, in particular *Brachyspira hyodysenteriae* and from *Vibrio*, in particular *V. parahemolyticus* and *V. harveyi*, and the beneficial bacteria are preferably selected from lactic acid bacteria, in particular from lactobacilli and bifidobacteria.

In a preferred embodiment of the invention the amount of at least one pathogenic bacterium, in particular the amount of *C. perfringens*, is reduced by at least 0.5 log, more preferably by at least 1 log, 2 log, or 3 log.

Thus, a further subject of the current invention are also the strains, preparations and compositions of the current invention for inhibiting and/or decreasing the growth of pathogenic bacteria and/or for maintaining and/or increasing the growth of beneficial bacteria in an animal gut, wherein the pathogenic bacteria are preferably selected from *Clostridia*, in particular from *C. perfringens, C. difficile, C. novyi, C. septicum* and *C. colinum*, from *Listeria*, in particular from *L. monocytogenes, L. seeligeri* and *L. welshimeri*, from *Salmonella*, in particular *S. enterica* including the subspecies *enterica, arizonae, bongori* and in particular the serovars, *S. gallinarum, S. pullorum, S. typhimurium, S. enteritidis, S. cholerasuis, S. heidelberg* and *S. infantis*, from *Enterococci*, in particular *E. faecalis, E. faecium* and *E. cecorum*, from *Staphylococci*, in particular *S. aureus*, from *Aeromonas*, from Streptococci, in particular *S. suis* and *S. gallinaceus*, from *Campylobacter*, in particular *C. jejuni* and *C. coli*, from *Escherichia coli*, from *Haemophilus*, in particular *Haemophilus parasuis*, from *Brachyspira*, in particular *Brachyspira hyodysenteriae* and from *Vibrio*, in particular *V. parahemolyticus* and *V. harveyi*, and the beneficial bacteria are preferably selected from lactic acid bacteria, in particular from lactobacilli and bifidobacteria.

The occurrence and/or increased growth of the pathogenic bacteria does or can lead to the outbreak of certain diseases. For example the occurrence and/or increased growth of *Clostridium perfringens* can lead to the outbreak of gut diseases, in particular to the outbreak of necrotic enteritis in swine and poultry. The occurrence and/or increased growth of *C. perfringens* can also lead to the outbreak of further diseases like bacterial enteritis, gangrenous dermatitis and colangiohepatitis. Even the mildest form of infection by *C. perfringens* can already be accompanied by diarrhea, which results in wet litter and by that may lead to secondary diseases like foot pad dermatitis. While *C. perfringens* type C generally is considered to be the primary cause of necrotic enteritis and necrohemorrhagic enteritis in piglets, type A has been linked to enteric disease in suckling and feeding pigs with mild necrotic enterocolitis and villous atrophy.

*Clostridium difficile* is an important emerging pathogen that causes diarrhea primarily in neonatal swine. Affected piglets may have dyspnea, abdominal distention, and scrotal edema.

*Staphylococcus aureus* subsp. *aureus* can cause bumblefoot in chickens, streptococcal mastitis in sows and it is capable of generating toxins that produce food poisoning in the human body.

*E. cecorum* is known to cause lameness, arthritis and osteomyelitis in broilers usually caused by an inflammation of a joint and/or bone tissue. Further *E. cecorum* can cause an inflammation of the pericardium.

*S. gallinaceus* can cause septicaemia in poultry. The gross lesions included splenomegaly, hepatomegaly, renomegaly and congestion. Multiple areas of necrosis and/or infarction in the liver and spleen associated with valvular endocarditis were also observed.

*C. coli* is a foodborne bacterium, most people usually get infected by eating pig meat that contained the bacteria. It causes gastroenteritis and acute enterocolitis in humans, and also of acute diarrheal illnesses. Pigs are the main host, but it can also infect humans, avian species and a wide range of other animals.

*S. suis* is an important pathogen in pigs and one of the most important causes of bacterial mortality in piglets after weaning causing septicemia, meningitis and many other infections.

Pathogens can cause further diseases like polyarthritis, fibrinous polyserositis, post-weaning enteric disorders like post-weaning diarrhea and edema disease and swine dysentery.

A further subject of the current invention is therefore also a therapeutic composition comprising the strains and/or compositions of the current invention as mentioned before.

A preferred subject in this context is therefore a therapeutic composition for treatment and/or prevention of necrotic enteritis and necrohemorrhagic enteritis, in particular sub-clinical necrotic enteritis and necrohemorrhagic enteritis, in animals, preferably swine or poultry, comprising the strains and/or compositions of the current invention as mentioned before.

Another preferred subject in this context is therefore a therapeutic composition for treatment and/or prevention of bacterial enteritis, gangrenous dermatitis, colangiohepatitis, clostridiosis, diarrhea, dyspnea, abdominal distention, scrotal edema, bumblefoot, foot pad dermatitis, streptococcal mastitis, lameness, arthritis, polyarthritis, fibrinous polyserositis, post-weaning enteric disorders like post-weaning diarrhea and edema disease, dysentery, osteomyelitis, inflammation of joints and/or bone tissue, inflammation of the pericardium, splenomegaly, hepatomegaly, renomegaly, congestion, necrosis, infarction in the liver or spleen, valvular endocarditis, septicemia and/or meningitis, in animals, preferably in swine or poultry, comprising the strains and/or compositions of the current invention as mentioned before.

A further subject of the current invention is therefore also the treatment and/or prevention of a disease, in particular of a gut disease, preferably of necrotic enteritis or necrohemorrhagic enteritis, in particular of sub-clinical necrotic enteritis or sub-clinical necrohemorrhagic enteritis, in swine or poultry, wherein a strain and/or composition and/or preparation of the current invention is administered to an animal in need thereof.

A further subject of the current invention is therefore also the treatment and/or prevention of a disease, preferably a disease of swine or poultry, selected from bacterial enteritis, gangrenous dermatitis, colangiohepatitis, clostridiosis, diarrhea, dyspnea, abdominal distention, scrotal edema, bumblefoot, foot pad dermatitis, streptococcal mastitis, lameness, arthritis, polyarthritis, fibrinous polyserositis, post-weaning enteric disorders like post-weaning diarrhea and edema disease, dysentery, osteomyelitis, inflammation of joints and/or bone tissue, inflammation of the pericardium, splenomegaly, hepatomegaly, renomegaly, congestion, necrosis, infarction in the liver or spleen, valvular endocarditis, septicemia and/or meningitis, wherein a strain and/or composition and/or preparation of the current invention is administered to an animal in need thereof.

The strains and/or preparations and/or compositions of the current invention can be administered to animals in feed and/or drinking water over multiple days throughout the animal's life or during particular stages or portions of the animal's life. For example, the strains and/or compositions can be administered only in a starter diet or only in a finisher diet of farm animals.

A particular subject of the current invention is also a method of enhancing the health of human beings and/or of improving the general physical condition of human beings and/or of increasing the disease resistance of human beings and/or of increasing the immune response of human beings and/or of establishing or maintaining a healthy gut microflora in human beings, wherein the strains and/or preparations of the current invention or the compositions of the current invention, which comprise such strain(s), are administered to human beings.

A further subject of the current invention is therefore also the use of strains and/or preparations and/or compositions of the current invention for enhancing the health of human beings and/or for improving the general physical condition of human beings and/or for increasing the disease resistance of human beings and/or for increasing the immune response of human beings and/or for establishing or maintaining a healthy gut microflora in human beings, wherein the strains and/or preparations of the current invention or the compositions of the current invention, which comprise such strain (s), are administered to human beings.

The compositions of the present invention, in particular the feed, food and pharmaceutical compositions as well as the drinking or rearing water, preferably comprise the strains of the current invention and are administered to animals at a rate of about $1 \times 10^3$ to about $2 \times 10^{12}$ CFU/g feed or ml water, in particular in a rate of about $1 \times 10^3$ or about $1 \times 10^4$ or about $1 \times 10^5$ or about $1 \times 10^6$ or about $1 \times 10^7$ or about $1 \times 10^8$ or about $1 \times 10^9$ or about $1 \times 10^{10}$ or about $1 \times 10^{11}$ or about $1 \times 10^{12}$ CFU/g feed or ml water, preferably in an amount of about $1 \times 10^4$ to about $1 \times 10^{10}$ CFU/g feed or ml water, more preferably in an amount of $1 \times 10^4$ to $1 \times 10^7$ CFU/g feed or ml water.

Correspondingly, preferred amounts of the strains and/or preparations of the current invention in the feed, food and water compositions of the current invention range preferably from 0.1 wt.-% to 10 wt.-%, more preferably from 0.2 wt.-% to 5 wt.-%, in particular from 0.3 wt.-% to 3 wt.-%.

The methods of the present invention may be used for all kind of animals, in particular all kind of non-human and non-insect animals, more preferably all kind of vertebrates such as mammals, aquatic animals and birds.

Animals that may benefit from the current invention include but are not limited to farm animals, pets, exotic animals, zoo animals, aquatic animals, animals used for sports, recreation or work.

Pets are preferably selected from dogs, cats, domestic birds and domestic exotic animals.

Aquatic animals are preferably selected from finfish and crustaceans which are preferably intended for human nutrition. These include, in particular, carp, tilapia, catfish, tuna, salmon, trout, barramundi, bream, perch, cod, shrimps, lobster, crabs, prawns and crayfish. Preferred types of salmon in this context are the Atlantic salmon, red salmon, masu salmon, king salmon, keta salmon, coho salmon, Danube salmon, Pacific salmon and pink salmon.

Further preferred aquatic animals are farming fish which are subsequently processed to give fish meal or fish oil. In this connection, the fish are preferably herring, pollack, menhaden, anchovies, capelin or cod.

In a further preferred embodiment, the animals are farm animals, which are raised for consumption or as food-producers, such as poultry, swine and ruminants.

The poultry may be selected from productive or domestic poultry, but also from fancy poultry or wild fowl.

Preferred productive poultry in this context are chickens, turkeys, ducks and geese. The productive livestock in this context is preferably poultry optimized for producing young stock or poultry optimized for bearing meat.

Preferred fancy poultry or wild fowl are peacocks, pheasants, partridges, chukkars, guinea fowl, quails, capercaillies, grouse, pigeons and swans, with quails being especially preferred.

Further preferred poultry are ratites, in particular ostriches and emus, as well as parrots.

Ruminants according to the current invention are preferably selected from cattle, goat and sheep. In one embodiment, the compositions of this invention may be fed to preruminants to enhance their health and, in particular, to decrease the incidence of diarrhea in these animals Preruminants are ruminants, including calves, ranging in age from birth to about twelve weeks.

The compositions of the current invention may comprise at least one carrier or typical feed ingredients or combinations thereof.

Suitable carriers are inert formulation ingredients added to improve recovery, efficacy, or physical properties and/or to aid in packaging and administration. Such carriers may be added individually or in combination. These carriers may be selected from anti-caking agents, anti-oxidation agents, bulking agents, and/or protectants. Examples of useful carriers include polysaccharides (in particular starches, maltodextrins, methylcelluloses, gums, chitosan and/or inulins), protein sources (in particular skim-milk powder and/or sweet-whey powder), peptides, sugars (in particular lactose, trehalose, sucrose and/or dextrose), lipids (in particular lecithin, vegetable oils and/or mineral oils), salts (in particular sodium chloride, sodium carbonate, calcium carbonate, chalk, limestone, magnesium carbonate, sodium phosphate, calcium phosphate, magnesium phosphate and/or sodium citrate), and silicates (in particular clays, in particular beolite clay, amorphous silica, fumed/precipitated silicas, zeolites, Fuller's earth, baylith, clintpolite, montmorillonite, diatomaceous earth, talc, bentonites, and/or silicate salts like aluminium, magnesium and/or calcium silicate). Suitable carriers for animal feed additives are set forth in the American Feed Control Officials, Inc.'s Official Publication, which publishes annually. See, for example Official Publication of American Feed Control Officials, Sharon Krebs, editor, 2006 edition, ISBN 1-878341-18-9. The carriers can be added after concentrating the fermentation broth and/or during and/or after drying. Preferred carriers according to the invention are selected from calcium carbonate, diatomaceous earth and vegetable oil.

A preferred embodiment of the current invention are concentrate compositions, in particular feed additive compositions, i.e. compositions suitable for preparing a feed composition, which comprise at least one strain of the current invention and at least one carrier as mentioned before, wherein the at least one strain is preferably comprised in an amount of 0.1 to 10 wt.-%, more preferably in an amount of 0.2 to 5 wt.-%, in particular in an amount of 0.3 to 3 wt.-%, above all in an amount of 0.4 to 2.2 wt.-%, and the at least one carrier is preferably comprised in an amount of at least 90 wt.-%, preferably in an amount of 90 to 99.9 wt.-%, more preferably in an amount of 95 to 99.8 wt.-%, in particular in an amount of 97 to 99.7 wt.-%, above all in an amount of 97.8 to 99.6 wt.-%, and wherein the carrier consists preferably substantially of limestone, in particular of limestone with smaller parts of diatomaceous earth and/or vegetable oil.

These preferred compositions of the current invention, which contain stabilized strains, can be used for the preparation of feed and pharmaceutical compositions as well as drinking and rearing water which preferably comprise the strains according to the invention in an amount as mentioned in the specification above. In a preferred embodiment 50 to 1000 grams of such a concentrate composition, in particular 50, 100, 250, 500 or 1000 grams of such a concentrate composition, are used per ton of feed, drinking or rearing water to provide compositions which can be used for feeding animals. These concentrate compositions preferably comprise at least one strain of the current invention in an amount of $1 \times 10^9$ to $2 \times 10^{11}$ CFU, in particular $2 \times 10^9$ to $1 \times 10^{11}$ CFU, per g of the concentrate composition.

Starting from these concentrate compositions, feed and food compositions can be prepared by mixing the concentrate compositions with typical feed or food ingredients, respectively.

Suitable typical animal feed ingredients which may be contained in the compositions according to the invention and/or used in the preparation of feed compositions starting from concentrate compositions according to the invention include one or more of the following: proteins, carbohydrates, fats, further probiotics, prebiotics, enzymes, vitamins, immune modulators, milk replacers, minerals, amino acids, coccidiostats, acid-based products and/or medicines, such as antibiotics.

Carbohydrates containing components which may be used according to the invention are for example forage, roughage, wheat meal, sunflower meal or soya meal, and mixtures thereof.

Proteins containing components which may be used according to the invention are for example soya protein, pea protein, wheat gluten or corn gluten, and mixtures thereof.

Fats containing components which may be used according to the invention are in particular oils, of both animal and plant origin, like vegetable oils, for example soya bean oil, rapeseed oil, sunflower seed oil, flaxseed oil or palm oil, fish oil, and mixtures thereof.

Proteins containing components which additionally contain fats which may be used according to the invention are for example fish meal, krill meal, bivalve meal, squid meal or shrimp shells, as well as combinations thereof.

Further probiotics (DFM) which may be used according to the invention in combination with the strains and preparations of the invention are preferably bacteria selected from the species *Bacillus subtilis, Bacillus licheniformis, Bacillus lentus, Bacillus pumilus, Bacillus laterosporus, Bacillus coagulans, Bacillus alevi, Bacillus cereus, Bacillus badius, Bacillus thurigiensis, Enterococcus faecium,* and *Pediococcus acidilactici.* Preferred examples are *Bacillus subtilis* DSM 32539 (as deposited with the DSMZ on Jun. 14, 2017 under the provisions of the Budapest Treaty on the International Recognition of the Deposit of Microorganisms for the Purpose of Patent Procedure) and derivatives thereof, *Bacillus licheniformis* DSM 32314 and *Bacillus subtilis* DSM 32315 (both deposited with the DSMZ on May 12, 2016 under the provisions of the Budapest Treaty on the International Recognition of the Deposit of Microorganisms for the Purpose of Patent Procedure) and derivatives thereof, *Bacillus subtilis* PB6 (as described in U.S. Pat. No. 7,247,299 and deposited as ATCC Accession No. PTA-6737), which is sold by Kemin under the trademark CLOSTAT®, *Bacillus subtilis* C-3102 (as described in U.S. Pat. No. 4,919,936 and deposited as FERM BP-1096 with the Fermentation Research Institute, Agency of Industrial Science and Technology, in Japan), sold by Calpis as CALSPORIN®, *Bacillus subtilis* DSM 17299, as sold by Chr. Hansen under the trademark GalliPro®, *Bacillus licheniformis* DSM 17236, as sold by Chr. Hansen under the trademark GalliProTect®, a mixture of *Bacillus licheniformis* DSMZ 5749 and *Bacillus subtilis* DSMZ 5750 spores, as sold by Chr. Hansen under the trademark BioPlus® YC, *B. subtilis* DSM 29784, as sold by Adisseo/Novozymes under the trademark Alterion®, *Bacillus subtilis,* as sold by Chr. Hansen under the trademark PORCBOOST®, or *Bacillus coagulans* strains as described in U.S. Pat. No. 6,849,256. Other non-*Bacillus* probiotics, such as *Saccharomyces cerevisiae, Pichia* pastor's, *Aspergillus niger, Aspergillus oryzae,* or *Hansenula,* may also be used in compositions of the present invention. In particular in food compositions further probiotics which are known to be useful to the human health may be used such as lactic acid producing bacteria, in particular lactobacilli, or Bifidobacteria. If said further probiotics are not formulated as part of the compositions of the present invention, they may be administered together (either at the same time or at different times) with the compositions of the present invention.

Prebiotics which may be used according to the invention are preferably oligosaccharides, in particular selected from galactooligosaccharides, silayloligosaccharides, lactulose, lactosucrose, fructooligosaccharides, palatinose or isomaltose oligosaccharides, glycosyl sucrose, maltooligosaccharides, isomaltooligosaccharides, cyclodextrins, gentiooligosaccharides, soybean oligosaccharides, xylooligosaccharides, dextrans, pectins, polygalacturonan, rhamnogalacturonan, mannan, hemicellulose, arabinogalactan, arabinan, arabinoxylan, resistant starch, mehbiose, chitosan, agarose, inulin, tagatose, polydextrose, and alginate.

Enzymes which may be used in feed compositions according to the invention and which may aid in the digestion of feed, are preferably selected from phytases (EC 3.1.3.8 or 3.1.3.26), xylanases (EC 3.2.1.8), galactanases (EC 3.2.1.89), galactosidases, in particular alpha-galactosidases (EC 3.2.1.22), proteases (EC 3.4), phospholipases, in particular phospholipases A1 (EC 3.1.1.32), A2 (EC 3.1.1.4), C (EC 3.1.4.3), and D (EC 3.1.4.4), lysophospholipases (EC 3.1.1.5), amylases, in particular alpha-amylases (EC 3.2.1.1); lysozymes (EC 3.2.1.17), glucanases, in particular beta-glucanases (EC 3.2.1.4 or EC 3.2.1.6), glucoamylases, cellulases, pectinases, or any mixture thereof.

Examples of commercially available phytases include Bio-Feed™ Phytase (Novozymes), Ronozyme® P and HiPhos™ (DSM Nutritional Products), Natuphos™ (BASF), Finase® and Quantum® Blue (AB Enzymes), the Phyzyme® XP (Verenium/DuPont) and Axtra® PHY (DuPont). Other preferred phytases include those described in e.g. WO 98/28408, WO 00/43503, and WO 03/066847.

Examples of commercially available xylanases include Ronozyme® WX and G2 (DSM Nutritional Products), Econase® XT and Barley (AB Vista), Xylathin® (Verenium) and Axtra® XB (Xylanase/beta-glucanase, DuPont). Examples of commercially available proteases include Ronozyme® ProAct (DSM Nutritional Products).

Vitamins which may be used according to the invention are for example vitamin A, vitamin D3, vitamin E, vitamin K, e.g., vitamin K3, vitamin B12, biotin, choline, vitamin B1, vitamin B2, vitamin B6, niacin, folic acid and panthothenate, e.g., Ca-D-panthothenate, or combinations thereof.

Immmune modulators which may be used are for example antibodies, cytokines, spray-dried plasma, interleukins, or interferons, or combinations thereof.

Minerals which may be used according to the invention are for example boron, cobalt, chloride, chromium, copper, fluoride, iodine, iron, manganese, molybdenum, selenium, zinc, calcium, magnesium, potassium, or sodium, or combinations thereof.

Amino acids which may be used according to the invention are for example lysine, alanine, threonine, methionine or tryptophan, or combinations thereof.

Thus, a further embodiment of the current invention is a method of preparing an animal feed composition comprising mixing at least one strain and/or at least one preparation and/or at least one concentrate composition of the current invention, in particular in an amount effective to enhance animal health, in particular gut health, with feed ingredients, such as proteins, lipids and/or carbohydrates, and optionally further beneficial substances, preferably as mentioned before, to provide a feeding product. This method may comprise for example also a pelleting step.

Standard pelleting processes known to those of skill in the art may be used, including extrusion processing of dry or semi-moist feeds. Preferred pelleting temperatures are between about 65° C. and about 120° C.

The strains and compositions of the present invention can be obtained by culturing the strains of the current invention according to methods well known in the art, including by using the media and other methods as described for example in U.S. Pat. No. 6,060,051, EP0287699 or US2014/0010792. Conventional large-scale microbial culture processes include submerged fermentation, solid state fermentation, or liquid surface culture. Towards the end of fermentation, as nutrients are depleted, the cells of the strains begin the transition from growth phase to sporulation phase, such that the final product of fermentation is largely spores, metabolites and residual fermentation medium. Sporulation is part of the natural life cycle of these strains and is generally initiated by the cell in response to nutrient limitation. Fermentation is configured to obtain high levels of colony forming units of the *Bacillus subtilis* cells and to promote sporulation. The bacterial cells, spores and metabolites in culture media resulting from fermentation may be used directly or concentrated by conventional industrial methods, such as centrifugation, tangential-flow filtration, depth filtration, and evaporation. The concentrated fermentation broth may be washed, for example via a diafiltration process, to remove residual fermentation broth and metabolites.

The fermentation broth or broth concentrate can be dried with or without the addition of carriers using conventional drying processes or methods such as spray drying, freeze drying, tray drying, fluidized-bed drying, drum drying, or evaporation. The resulting dry products may be further processed, such as by milling or granulation, to achieve a specific particle size or physical format. Carriers, as described above, may also be added post-drying.

Preparations of the strains of the current invention may be cell-free preparations or preparations containing cell debris or preparations containing a mixture of intact cells and cell debris. Cell-free preparations of the strains of the current invention can be obtained for example by centrifugation and/or filtration of fermentation broth. Depending on the technique used, these cell-free preparations may not be completely devoid of cells, but may still comprise a smaller amount of cells. As the cells secret compounds like metabolites, enzymes and/or peptides into the surrounding medium, the supernatant of the cells comprises a mixture of such compounds, in particular metabolites, enzymes and/or peptides, as secreted by the cells. Thus, in a preferred embodiment of the invention, the preparation of the strains is a supernatant of the fermentation broth.

Compositions comprising cell debris of the strains may be obtained by rupturing the cells applying techniques as known to those of skill in the art, for example by mechanical means or by applying high pressure. Depending on the degree of force applied, a composition comprising only ruptured cells or a composition comprising a mixture of cell debris and intact cells is obtained. Homogenization of the cells may be realized for example by utilizing a French cell press, sonicator, homogenizer, microfluidizer, ball mill, rod mill, pebble mill, bead mill, high pressure grinding roll, vertical shaft impactor, industrial blender, high shear mixer, paddle mixer, and/or polytron homogenizer. Suitable alternatives are enzymatic and/or chemical treatment of the cells.

Cell-free preparations of the current invention comprise also preparations which are obtained by first rupturing the cells by applying techniques as mentioned before and subsequently removing the cell debris and the remaining intact cells. Removing of the cell debris and remaining intact cells can be carried out in particular by centrifugation and/or filtration.

The preparations of the strains of the current invention may comprise as active compounds at least one metabolite, preferably a mixture of metabolites, as further described below, and/or at least one enzyme selected from proteases, in particular subtilisin, xylanases and/or cellulases, and/or at least one peptide, and/or combinations thereof.

A preparation containing an effective mixture of metabolites as contained in the strains of the current invention and/or as contained in the cell preparations as mentioned before, can be obtained for example according to the methods set forth in U.S. Pat. No. 6,060,051. In particular the preparation can be obtained by precipitating the metabolites as contained in the preparations mentioned before by using organic solvents like ethyl acetate and subsequent redissolving of the precipitated metabolites in an appropriate solvent. The metabolites may subsequently be purified by size exclusion filtration that groups metabolites into different fractions based on molecular weight cut-off.

The preparation containing an effective mixture of metabolites of the current invention preferably comprises at least five, more preferably at least 6, 7, 8, 9, 10 or 12, in particular all metabolites of the strains of the invention. The content of metabolites of the strain DSM 32540 is depicted in Table 5.1. The metabolites possess preferably a molecular weight of between 400 and 4000 Dalton, more preferably of between 500 and 3500 Dalton.

Preferably according to the invention always an effective amount of the strains and/or preparations and/or compositions of the current invention is used in the embodiments of the current invention. The term "effective amount" refers to an amount which effects at least one beneficial effect to an animal and/or to the environment, in particular with respect to the features as already mentioned before, in comparison to an animal that has not been administered the strains and/or preparations and/or compositions of the current invention, but besides that has been administered the same diet (including feed and other compounds).

In case of therapeutic applications preferably a therapeutic amount of the strains and/or preparations and/or compositions of the current invention is used. The term "therapeutic amount" refers to an amount sufficient to ameliorate, reverse or prevent a disease state in an animal. Optimal dosage levels for various animals can easily be determined by those skilled in the art, by evaluating, among other things, the composition's ability to (i) inhibit or reduce pathogenic bacteria in the gut at various doses, (ii) increase or maintain levels of beneficial bacteria and/or (iii) enhance animal health, in particular gut health, at various doses.

WORKING EXAMPLES

Example 1. Strain Characteristics Relevant to Survival in the Gastrointestinal Tract

*Bacillus subtilis* strains were screened from various environmental samples in order to obtain a superior strain as animal direct-fed microbial/probiotic. As the strain is intended to reach its full potential in the intestine of the target animal, the strain was pre-screened to withstand various environmental and gut related conditions. Strain spores were generated (Nicholson and Setlow 1990), washed and incubated at 80° C. for 20 minutes (pasteurization), then titrated in logarithmic/1 in 10 dilutions using veal infusion broth agar (VI, Difco™, no. 234420, Becton Dickinson GmbH, Heidelberg, Germany). The second highest dilution prior to no growth was stored at −80° C. and used as standardized starting point for all further assessments from spore state. To simulate gastric passage (Argenzio 2004a; Trampel and Duke 2004), survival of acid exposure was assessed based on Larsen et al. (2014). Growth of vegetative cells was furthermore assessed at low pH indicating growth under stomach/proventriculus and gizzard conditions, as well as in presence of up to 4 mM bile (B8631, CAS 8008-63-8, Sigma-Aldrich) at pH 7 in order to confirm strain growth at the proximal part of the small intestine right after clearance of the stomach or gizzard (Argenzio 2004b; Trampel and Duke 2004). Strain fitness in the anaerobe intestine (Argenzio 2004b; Trampel and Duke 2004) was assessed by inoculating standardized spore solutions under anaerobic conditions (AnaeroPak™, Thermo Fisher Scientific) in VI medium supplemented with 2.5 mM $KNO_3$ (Glaser et al. 1995). Furthermore was the anaerobe proteolytic and cellulytic activity of strains assessed on VI agar plates supplemented with 1% skim milk powder (70166, Sigma-Aldrich) or 0.1% water insoluble AZCL-HE cellulose (I-AZCEL, Megazyme International, Bray, Ireland). Furthermore the aerobe cellulytic activity of strains was assessed using VI agar supplemented with 0.1% water insoluble AZCL-HE cellulose (I-AZCEL, Megazyme International, Bray, Ireland). After 24 h under aerobe conditions, a blue coloration of agar indicated cellulase activity.

Osmotic stress, as also found in the gut (Argenzio 2004b; Trampel and Duke 2004), was assessed by determining growth on VI agar with addition of 10 wt.-% NaCl (den Besten et al. 2009). Finally, spore heat stability was assessed to determine pelleting stability by exposing spores to 99° C. for 20 min (Palop et al. 1996) and subsequent inoculation on VI agar.

*Bacillus subtilis* strain DSM 32540 survived simulated gastric passage, growth of the strain was observed starting at pH 6. Strain DSM 32540 grew anaerobically and was able to degrade water-insoluble cellulose and protein under anaerobic conditions. Further, it was able to degrade water-insoluble cellulose under aerobic conditions. Strain DSM 32540 was able to grow in presence of 2 and 4 mM bile, in presence of 0.3 wt.-% porcine bile and in presence of 0.3 wt.-% chicken bile as well as in presence of 10 wt.-% NaCl. Strain DSM 32540 reached an average spore count of $9.1 \times 10^8$ CFU/mL, and spores of strain DSM 32540 were viable after exposure to 99° C. for 20 min.

REFERENCES

Argenzio, R. A. (2004a). Secretion of the Stomach and Accessory Glands, p. 405-418. In: Reece, W. O. (ed.), Duke's Physiology of Domestic Animals; Twelfth Edition, Chapter 25; Cornell University Press, Ithaca, New York, USA.

Argenzio, R. A. (2004b). Digestive and Absorptive Functions of the Intestines, p. 419-437. In: Reece, W. O. (ed.), Duke's Physiology of Domestic Animals; Twelfth Edition, Chapter 26; Cornell University Press, Ithaca, New York, USA.

Dawson, R. M. C.; Elliot, D. C.; Elliot, W. H.; Jones, K. M. (1986). Data for Biochemical Research; $3^{rd}$ edition, Oxford Science Publishing, United Kingdom.

Den Besten H M W, Mols M, Moezelaar R, Zwietering M H, Abee T. (2009). Phenotypic and transcriptomic analyses of mildly and severely salt-stressed *Bacillus cereus* ATCC 14579 cells. Appl Environ Microbiol. 75:4111-9.

Glaser, P., A. Danchin, F. Kunst, P. Zuber, and M. M. Nakano. (1995). Identification and isolation of a gene required for nitrate assimilation and anaerobic growth of *Bacillus subtilis*. J. Bacteriol. 177:1112-1115

Nicholson W. L., Setlow P. Sporulation, germination and outgrowth. In: Harwood C R, Cutting S M, editors. Molecular biological methods for *Bacillus*. Chichester, England: John Wiley & Sons Ltd.; 1990. pp. 27-74.

Palop, A., Raso, J., Pagan, R., Condon, S. and Sala, F. J. (1996). Influence of pH on heat resistance of *Bacillus*

*licheniformis* in buffer and homogenized foods. International Journal of Food Microbiology 29, 1-10.

Trampel, D. W. and Duke, G. E. (2004). Avian Digestion, p. 488-500. In: Reece, W. O. (ed.), Duke's Physiology of Domestic Animals; Twelfth Edition, Chapter 29; Cornell University Press, Ithaca, New York, USA.

Example 2. Comparative Strain Performance Relative to State of the Art Direct-Fed Microbial (DFM)/Probiotic for Animal Nutrition—Quantitative Assessment of Bile Tolerance In order to assess the competitiveness of the *Bacillus subtilis* strain DSM 32540 selected from example 1, benchmarked analysis was performed using commercially available *Bacillus subtilis* strain DSM 17299 and/or *Bacillus licheniformis* strain DSM 17236. Readiness of strains to perform in the proximal small intestine in presence of bile at neutral pH right after gastric passage (Argenzio 2004b; Trampel and Duke 2004) was determined by strain growth in VIB media with addition 0.3 wt.-% porcine bile (Sigma Aldrich). Overnight culture with 50 uL candidate strain cell suspension and 10 mL VIB in 100 mL conical flask was incubated at 37° C. and 200 rpm, then approximately 50 uL of overnight culture was transferred to 100 well honeycomb plates (Oy Growth Curves Ab Ltd, former Thermo Labsystems, Helsinki, Finland) with 1 mL VIB at pH 7 with 0.3 wt.-% porcine bile in order to obtain OD 0.2 per mL.

Strain specific growth at 37° C. and 200 rpm was observed for 48 h with OD determined every 15 min using Bioscreeen C MBR with BioLink software package (Oy Growth Curves Ab Ltd). Quantitative assessment for each strain was compared as area under the curve between 0-5 h (AUC5, in OD×time in h), area under the curve between 0-10 h (AUC10 in OD×time in h), and time until strains reached its maximum optical density (Tmax in h). Results can be found in Table 2.1.

TABLE 2.1

Growth of *Bacillus subtilis* strain DSM 32540 and benchmark strains DSM 17299 and DSM 17236 in presence of 0.3 wt.-% porcine bile.

| Strain | Tmax | AUC5 | AUC10 | AUC30 |
|---|---|---|---|---|
| DSM 32540 | 9.25 | 3.33 | 10.35 | 31.68 |
| DSM 17299 | 26 | 1.57 | 3.68 | 22.67 |
| DSM 17236 | 36.75 | 1.19 | 3.27 | 15.02 |

AUC5, area under the curve between time point 0 and 5 h in optical density×h; AUC10, area under the curve between time point 0 and 10 h in optical density×h; Tmax, time in h until maximum optical density was reached.

In direct comparison, strain DSM 32540 reached its maximum OD in presence of 0.3 wt.-% porcine bile 16.75 h faster than the benchmark strain DSM 17299 and 27.5 h faster than DSM 17236. In addition, strain DSM 32540 grew 2.7 times faster during the first 5 hours, 3.2 times faster during the first 10 h and 2.1 times faster during the first 30 h compared to the growth of DSM 17236, respectively. Furthermore DSM 32540 is able to grow in the presence of 0.3% chicken bile.

REFERENCES

Argenzio, R. A. (2004b). Digestive and Absorptive Functions of the Intestines, p. 419-437. In: Reece, W. O. (ed.), Duke's Physiology of Domestic Animals; Twelfth Edition, Chapter 26; Cornell University Press, Ithaca, New York, USA.

Trampel, D. W. and Duke, G. E. (2004). Avian Digestion, p. 488-500. In: Reece, W. O. (ed.), Duke's Physiology of Domestic Animals; Twelfth Edition, Chapter 29; Cornell University Press, Ithaca, New York, USA.

Example 3. Comparative Strain Performance Relative to State of the Art Direct-Fed Microbial (DFM)/Probiotic for Animal Nutrition—Growth in Presence of Short Chain Fatty Acids (SCFA)

Comparative growth of strains DSM 32540 and DSM 17299 was assessed in presence of short chain fatty acids as those are observed in the gut with increasing importance towards the large intestine (Argenzio 2004b; Trampel and Duke 2004). Tests were initiated using standardized spore solution as described in example 1 testing aerobe growth in VI medium at 37° C. and pH 6, read-out parameter was growth versus no growth. For this test, VI medium was adjusted to pH 6 using McIlvaine buffer (Palop et al. 1996) and subsequently supplemented with 0.05% acetic acid (HA, 537020, CAS 64-19-7, Sigma-Aldrich), 0.05% propionic acid (HP, P1386, CAS 79-09-4, Sigma-Aldrich) or 0.2% lactic acid (HL, W261106, CAS 50-21-5, Sigma-Aldrich). Results can be found in Table 3.1.

TABLE 3.1

Assessment of growth of *Bacillus subtilis* strains DSM 32540 and benchmark strain DSM 17299 in presence of short chain fatty acids at pH 6.

| Strain ID | Acetic acid | Propionic acid | Lactic acid |
|---|---|---|---|
| DSM 32540 | Yes | Yes | Yes |
| DSM 17299 | No growth | No growth | No growth |

*Bacillus subtilis* strain DSM 32540 was able to grow at pH 6 in the presence of acetic, propionic and lactic acid, whereas strain DSM 17299 was unable to grow from spore stage under these conditions.

REFERENCES

Argenzio, R. A. (2004b). Digestive and Absorptive Functions of the Intestines, p. 419-437. In: Reece, W. O. (ed.), Duke's Physiology of Domestic Animals; Twelfth Edition, Chapter 26; Cornell University Press, Ithaca, New York, USA.

Palop, A., Raso, J., Pagan, R., Condon, S. and Sala, F. J. (1996). Influence of pH on heat resistance of *Bacillus licheniformis* in buffer and homogenized foods. International Journal of Food Microbiology 29, 1-10.

Trampel, D. W. and Duke, G. E. (2004). Avian Digestion, p. 488-500. In: Reece, W. O. (ed.), Duke's Physiology of Domestic Animals; Twelfth Edition, Chapter 29; Cornell University Press, Ithaca, New York, USA.

Example 4. Comparative Strain Performance Relative to State of the Art Direct-Fed Microbial (DFM)/Probiotic for Animal Nutrition—Quantitative Assessment of Enzymatic Activity Similar to test conducted in Example 2, strains DSM 32540, DSM 17299 and DSM 17236 were compared evaluating the respective aerobe xylanolytic activity. Xylanase activity was determined as described in Larsen et al. (2014). Analysis was performed in three independent runs, then averaged as milliunits per microliter solution.

TABLE 4.1

Xylanase activity of strains DSM 32540, DSM 17299 and DSM 17236.

| Strain ID | Xylanase activity (mU/mL) |
|---|---|
| DSM 32540 | 11.8 ± 0.3 |
| DSM 17299 | 11.8 ± 1.5 |
| DSM 17236 | 7.9 ± 1.3 |

In direct comparison, strain DSM 32540 has a 1.5 fold increased xylanase activity compared to benchmark strain pathogens inhibited in the respective media. For metabolite expression analysis, starter cultures were grown and tests performed as described in Scholz et al. (2011). From 10 mL Luria Bertami broth (LB, Thermo Fisher Scientific) culture grown for 24 h at 37° C. and 160 rpm in 100 mL flask, 100 uL were transferred to main culture. Main culture was grown either in 10 mL LB containing 0.2 mL/L KellyT trace metal solution (LBKelly, Scholz et al. 2011), or 10 mL Trypticase Soy Broth (Oxoid, Thermo Fisher Scientific) with 0.6% yeast extract (Y1625, CAS 8013-1-2, Sigma-Aldrich; resulting broth abbreviated TSBYE), both for 24 h at 37° C. at 160 rpm in 100 mL flask. Of the main culture, 4 mL were combined with 2 mL n-Butanol in 15 mL test tube, vortexed for 3 min, then sonicated for 15 min. After centrifugation for 1 min at 5000 rpm, organic phase was transferred, vacuum dried and analyzed using High-performance liquid chromatography—electrospray ionization mass spectrometry (HPLC-ESI-MS; Chen et al. 2006). Every sample was measured in two different modes, negative and positive mode, and mass spectra were acquired. Resulting peaks as similarly reported in Teo and Tan (2005) were converted to molecular mass in Da. Results for comparison can be found in Table 5.1.

TABLE 5.1

(a) Comparison of metabolites expressed by strains DSM 32540 and wildtype strain DSM 10 in LB-Kelly and TSBYE, respectively (n/d means not detected)

| Strain | 330 Da | 350 Da | 352 Da | 423 Da | 424 Da | 477 Da | 480 Da | 572 Da | 993 Da | 994 Da | 1008 Da | 1143 Da |
|---|---|---|---|---|---|---|---|---|---|---|---|---|
| DSM 10 | n/d | n/d | n/d | n/d | n/d | n/d | n/d | n/d | yes | n/d | yes | n/d |
| DSM 32540 | yes | yes | yes | yes | yes | yes | yes | yes | yes | yes | yes | yes |

TABLE 5.1

(b) Comparison of metabolites expressed by strains DSM 32540 and wildtype strain DSM 10 in LB-Kelly and TSBYE, respectively (n/d means not detected)

| Strain | 1022 Da | 1026 Da | 1036 Da | 1040 Da | 1050 Da | 1460 Da | 1462 Da | 1476 Da | 1489 Da | 1504 Da | 1505 Da | 3401 Da |
|---|---|---|---|---|---|---|---|---|---|---|---|---|
| DSM 10 | yes | n/d | yes | n/d | yes | yes | yes | yes | n/d | yes | n/d | yes |
| DSM 32540 | yes | yes | yes | yes | yes | yes | n/d | yes | yes | yes | yes | yes |

DSM 17236 and a similar xylanase activity compared to benchmark strain DSM 17299.

REFERENCE

Larsen, N., Thorsen, L., Kpikpi, E. N., Stuer-Lauridsen, B., Cantor, M. D., Nielsen, B., Brockmann, E., Derkx, E. M. F. and Jespersen, L. (2014). Characterization of *Bacillus* spp. strains for use as probiotic additives in pig feed. Applied microbiology and biotechnology, 98(3), 1105-1118.

Example 5. Comparative Strain Performance Relative to State of the Art Direct-Fed Microbial (DFM)/Probiotic for Animal Nutrition—Expression of Metabolites and Pathogen Inhibition Similar to tests conducted in Example 2, strains DSM 32540 and wildtype strain DSM 10 were compared evaluating the respective number of metabolites expressed and In addition, pathogen inhibition via *Bacillus subtilis* secondary metabolite production, as part of metabolites from table 5.1. but not closer investigated, was assessed using well diffusion antagonism tests (Parente et al. 1995).

A well diffusion antagonisms test with 7 different pathogens, *Clostridium perfringens, Clostridium difficile* DSM 1296, *Enterococcus* cecorum DSM 20683, *Staphylococcus aureus* subsp. *aureus* DSM 20231, *Streptococcus* gallinaceus DSM 15349, *Streptococcus suis* ATCC 43765 and *Campylobacter coli* ATCC 33559 was performed.

Three pathogenic *C. perfringens* candidates were tested being *C. perfringens* type strain ATCC 13124 from Teo and Tan (2005), as well as two pathogenic *C. perfringens* field isolates from swine, obtained from RIPAC-LABOR GmbH, Potsdam-Golm, Germany. The *C. perfringens* type C-strains from Ripac describe as follows: Strains BB-081_Cpe and BB-031_Cpe were isolated from necrotic enteritis positive swine digestive tract. Strain BB-081_Cpe is cpb2 positive (Songer et al. 2005) and netB negative and Strain BB-031_Cpe tested positive for β2-toxin (Allaart et al. 2012). Strain ATCC 13124 is known to be alpha-toxigenic Type A strain serving as a type strain for *Clostridia*.

*Clostridium difficile* is an important emerging pathogen that causes diarrhea primarily in neonatal swine (Songer et al. 200). Affected piglets may have dyspnea, abdominal lated with 100 uL of *Bacillus subtilis* DSM 32540 or DSM 17299 culture. After 24 h incubation under suitable conditions at 37° C., the zone of clearance in mm was determined measuring from the edge of the cut well to the border of the cleared lawn. Each colony was measured twice (horizontally, vertically), then averaged. The results can be found in the following tables.

TABLE 5.2

Comparison of *Bacillus subtilis* DSM 32540, DSM 17236 and DSM 17299 inhibitory capacity on pathogenic *Clostridium* strains in well diffusion antagonism assays on LB Kelly medium, values in mm clearance of pathogen.

| | Pathogen | | | |
| --- | --- | --- | --- | --- |
| Probiotic | *C. perfringens* ATCC 13124 | *C. perfringens* BB-081_Cpe | *C. perfringens* BB_031_Cpe | *C. difficile* DSM 1296 |
| DSM 32540 | 20.3 | 26.3 | 18.7 | 12.3 |
| DSM 17299 | 8 | 8 | 8 | n/d |
| DSM 17236 | 17 | 15.5 | 8 | 8 | distention, and scrotal edema. Diarrhea may not be present in all pigs affected. DSM 1296 is a known type strain for *C. difficile* and produces cytotoxin.

*Staphylococcus aureus* subsp. *aureus* can cause bumblefoot in chickens (McMullin 2004), streptococcal mastitis in sows (Contreras et al. 2011) and it is capable of generating toxins that produce food poisoning in the human body (2016 Centers for Disease Control and Prevention). DSM 20231 is a serotype 3 type strain.

*E. cecorum* is known to cause lameness, arthritis and osteomyelitis in broilers usually caused by an inflammation of a joint and/or bone tissue. Additional *E. cecorum* can cause an inflammation of the pericardium [Kense et al. 2011]. DSM 20683 was isolated from caecum of a chicken.

*S. gallinaceus* can cause septicaemia in poultry. The gross lesions included splenomegaly, hepatomegaly, renomegaly and congestion. Multiple areas of necrosis and/or infarction in the liver and spleen associated with valvular endocarditis were also observed [Collins et al. 2002].

*S. suis* is an important pathogen in pigs and one of the most important causes of bacterial mortality in piglets after weaning causing septicemia, meningitis and many other infections [Goyette-Desjardins et al. 2014]. ATCC 43765 belongs to Serological group: R; serovar 2 and was isolated from pigs.

*C. coli* is a foodborne bacterium, most people usually get infected by eating pig meat that contained the bacteria. It causes gastroenteritis and acute enterocolitis in humans, and also of acute diarrheal illnesses [Fitzgerald et al. 2007]. Pigs are the main host, but it can also infect humans, avian species and a wide range of other animals. ATCC 33559 was isolated from pig feces.

*Bacillus* strains were grown in 10 mL TSBYE (30 g/l TSB+6 g/l Yeast extract) or LB-Kelly (LB-Media supplemented with trace elements solution of DSMZ media 1032) for 16 h at 37° C. and 200 rpm in 100 mL shaking flask. The pathogenic strains were grown under suitable conditions as liquid culture to an optical density of 595 nm of at least 1, then 100 µl were spread with sterile spatula on the surface of agar plates. For *S. gallinaceus* BHI agar plates, all other pathogens TSBYE agar plates are used. Three 9 mm diameter wells were cut into the dried plates. 1st well was used as non-inoculated media control without culture, 2nd well was inoculated with 100 uL not-inhibiting *Bacillus* strain (*B. cereus* var. *toyoi*, NCIMB 40112), the 3rd well was inocu- The data show that DSM 32540 is able to inhibit the growth of *C. perfringens* and *S. difficile* very effectively, in particular in comparison to DSM 17299.

TABLE 5.3

Comparison of *Bacillus subtilis* DSM 32540, DSM 17236 and DSM 17299 inhibitory capacity on pathogenic *Staphylococcus, Streptococcus* and *Campylobacter* strains in well diffusion antagonism assays on LB Kelly medium, values in mm clearance of pathogen.

| | Pathogen | | | |
| --- | --- | --- | --- | --- |
| Probiotic | *S. aureus* subsp. *aureus* DSM 20231 | *S. gallinaceus* DSM 15349 | *S. suis* DSM 9682 | *C. coli* DSM 4689 |
| DSM 32540 | 21 | 21.8 | 30.4 | 28.4 |
| DSM 17299 | 8 | 8 | 13.5 | 8 |
| DSM 17236 | n/d | n/d | 20.7 | 8 |

The data show that DSM 32540 is able to inhibit the growth of *S. aureus* subsp. *aureus, S. gallinaceus, S. suis* and *C. coli* very effectively, in particular in comparison to DSM 17299.

TABLE 5.4

Comparison of *Bacillus subtilis* DSM 32540, DSM 17236 and DSM 17299 inhibitory capacity on pathogenic *Enterococcus cecorum* in well diffusion antagonism assays on TSBYE medium, values in mm clearance of pathogen.

| Probiotic | Pathogen *E. cecorum* DSM 20683 |
| --- | --- |
| DSM 32540 | 16.9 |
| DSM 17299 | 8 |
| DSM 17236 | 13.7 |

The data show that DSM 32540 is able to inhibit the growth of *E. cecorum* very effectively, in particular in comparison to DSM 17299.

REFERENCES

Teo, A. Y.-L. and Tan, H.-M. (2005). Inhibition of *Clostridium perfringens* by a novel strain of *Bacillus subtilis* from the gastrointestinal tracts of healthy chickens. Appl. Environm. Microbiol., 71:4185-90. Paul McMullin (2004) Chapter: *Staphylococcus aureus* subsp. *aureus* infections in chickens. Book: A pocket guide to poultry health and disease. Publisher: 5m Publishing.

Parente, E., Brienza, C., Moles, M., & Ricciardi, A. (1995). A comparison of methods for the measurement of bacteriocin activity. Journal of microbiological methods, 22(1), 95-108.

G A Contreras, J M Rodriguez (2011) Mastitis: Comparative Etiology and Epidemiology Journal of Mammary Gland Biology and Neoplasia, Volume 16, Issue 4, pp 339-356 (2016) U.S. Department of Health & Human Services (https://www.cdc.gov/foodsafety/diseases/staphylococca-l.html)

Allaart, J. G., de Bruijn, N. D., van Asten, A. J., Fabri, T. H., and Grone, A. (2012). NetB-producing and beta2-producing *Clostridium perfringens* associated with subclinical necrotic enteritis in laying hens in the Netherlands. Avian Pathol., 41:541-546 JG Songer, F A Uzal (2005) Clostridial Enteric Infections in Pigs. Volume: 17 issue: 6, page(s): 528-536 Journal of Veterinary Diagnostic Investigation Songer J G, Post K W, Larson D J, et al. (2000) Infection of neonatal swine with *Clostridium difficile*. Swine Health Prod. 2000; 8(4):185-189

MJ Kense, W J M Landman (2011) *Enterococcus cecorum* infections in broiler breeders and their offspring: molecular epidemiology. Avian Pathology, Volume 40, Issue 6

MD Collins, R A Hutson, E Falsen, E Ingana, M Bisgaard (2002) *Streptococcus gallinaceus* sp. nov., from chickens. International Journal of Systematic and Evolutionary Microbiology, 52, 1161-1164

G Goyette-Desjardins, J-P Auger, J Xu, M Segura, M Gottschalk (2014) *Streptococcus suis*, an important pig pathogen and emerging zoonotic agent an update on the worldwide distribution based on serotyping and sequence typing. Emerg Microbes Infect. 2014 June; 3(6):e45.

C Fitzgerald, I Nachamkin (2007). *Campylobacter* and *Arcobacter*. In P. R. Murray (Ed.), Manual of Clinical Microbiology (9th ed., pp. 933-946). Washington D.C.: ASM Press.

Example 6. Qualitative Assessment of Antioxidant Enzymatic Activity

The presence of reactive oxygen species during oxidative stress, which can be caused by stressful conditions as for example heat stress (Lin et al., 2006), can lead to a damage of DNA, proteins or lipids. Probiotics can support the host's oxidative defense system by increasing the antioxidant enzyme activities (Aluwong et al., 2013, Mishra et al., 2015). Therefore, the strain DSM 32540 was screened for antioxidant enzyme activities, in particular for superoxide dismutase and catalase activity. For the evaluation of catalase activity of grown biofilms of the strain, the strain was grown in LB medium supplemented with glucose for 15 hrs at 37° C. and 200 rpm in shaking flasks. The cultures were adjusted to an optical density $OD_{600}$ of 1.0 and 10 µl of the cultures were spotted onto TSBYE (30 g/l TSB+6 g/l Yeast extract) or LB-Kelly (LB-Media supplemented with trace elements solution of DSMZ media 1032) agar plates, which were incubated at 37° C. under aerobic conditions and at 37° C. under 0.2% oxygen for 15 hrs. 3% $H_2O_2$ (hydrogen peroxide solution 3%, Sigma-Aldrich®) was dropped onto the colonies and catalase activity was analyzed. The read out parameter was the production of 02 and $H_2O$ from $H_2O_2$ resulting in the formation of foam on the colonies.

24

TABLE 6.1

Assessment of catalase activity of colonies of *Bacillus subtilis* strain DSM 32540 grown as biofilm on LB-Kelly or TSBYE medium under aerobic conditions.

| Strain ID | TSBYE | LB-Kelly |
|---|---|---|
| DSM 32540 | Yes | Yes |

*Bacillus subtilis* strain DSM 32540 displayed catalase activity when grown under aerobic conditions.

TABLE 6.2

Assessment of catalase activity of colonies of *Bacillus subtilis* strain DSM 32540 grown as biofilm on LB-Kelly or TSBYE medium under 0.2% oxygen.

| Strain ID | TSBYE | LB-Kelly |
|---|---|---|
| DSM 32540 | Yes | Yes |

*Bacillus subtilis* strain DSM 32540 displayed catalase activity also when grown under 0.2% oxygen.

Catalase activity was analyzed in protein extracts obtained from planktonic cells grown under aerobic conditions as well. The strain DSM 32540 was grown for 15 hrs in LB medium containing glucose at 37° C. and 200 rpm in shaking flasks. 8 ml of the cell cultures were harvested by centrifugation for 10 min at 4° C. and 3000 rpm and the pellet was resuspended in PBS pH 7.3. Soluble cell extracts were obtained by using a ribolyser. The disrupted cells were centrifuged for 10 min at 4° C. and 13000 rpm and the supernatant was used for further steps. The protein concentration of the protein extracts was determined by the method of Bradford with bovine serum albumin as a standard (Bradford, 1976). The concentration of the protein extracts was adjusted with PBS pH 7.3, the protein extracts were mixed with native sample loading buffer (2×, VWR) and native gel electrophoresis (10% non-denaturing polyacrylamide gels, Biorad) was applied to separate the proteins at 4° C. Catalase activity in cell extracts from planktonic cells was then detected by staining the gel in a staining solution of 1% $FeCl_3$ and 1% $K3Fe(CN)_6$ (Woodbury et al., 1971). Catalase activity can be seen as bright bands.

| Strain ID | LB with glucose |
|---|---|
| DSM 32540 | Yes |

*Bacillus subtilis* strain DSM 32540 displayed catalase activity also under these specific conditions as tested.

Superoxide dismutase activity was analyzed in protein extracts from cells grown under aerobic conditions as well. Cell extracts were obtained by the method described above and proteins were separated by performing native gel electrophoresis at 4° C. Superoxide dismutase activity was detected by staining the gel with a nitroblue tetrazolium staining method adapted from Beauchamp and Fridovich (19711

| Strain ID | LB with glucose |
|---|---|
| DSM 32540 | Yes |

*Bacillus subtilis* strain DSM 32540 displayed superoxide dismutase activity under the conditions tested.

REFERENCES

Aluwong, T.; Kawu, M.; Raji, M.; Dzenda, T.; Govwang, F.; Sinkalu, V. and Ayo, J. (2013). Effect of Yeast Probiotic on Growth, Antioxidant Enzyme Activities and Malondialdehyde Concentration of Broiler Chickens. Antioxidants 2: 326-339

Beauchamp, C. and Fridovich, I. (1971). Superoxide dismutase: improved assays and an assay applicable to acrylamide gels. Anal. Biochem. 44: 276-287.

Bradford, M. M. (1976). A rapid and sensitive method for the quantitation of microgram quantities of proteins utilizing the principle of protein-dye binding. Anal. Biochem. 72: 248-254.

Lin, H.; Decuvpere, E. and Buyse, J. (2006). Acute heat stress incuces oxidative stress in broiler chickens. Comp. Biochem. Physiol. A. Mol. Integr. Physiol. 144: 11-17.

Mishra, V.; Shah, C.; Mokashe, N.; Chavan, R.; Yadav, H. and Prajapati, J. (2015). Probiotics as potential antioxidants: a systematic review. J. Agric. Food Chem 63: 3615-3626

Woodbury, W.; Spencer, A. K. and Stahmann, M. A. (1971). An improved procedure using ferricyanide for detecting catalase isozymes. Anal. Biochem. 44: 301-305.

Example 7. Detection of Lactate Production

It has been shown in in vitro studies that inhibition of pathogen replication can be mediated by low-molecular-weight substances (Oelschlager 2010). Top of this list are short chain fatty acids, e.g. lactic acid (Oelschlager 2010). Possible explanation for the inhibition of pathogens can be decreasing the pH by production of lactic acid (Fuller 1992). Lactic acid bacteria, which are also used as probiotic in animal feed are known to produce lactic acid as major end-product during fermentation of cabohydrates (Halasz 2009). It is shown that *B. subtilis* strain DSM 32540 can produce lactate in vitro.

*B. subtilis* strain DSM 32540 and *Bacillus toyonensis*—a probiotic *bacillus* known to produce lactic acid—were compared evaluating the anaerobe lactate production. Lactate production was determined as follows: Precultures of the strains were grown over night at 37° C. in 10 mL TSBYE (30 g/l TSB+6 g/l Yeast extract) under aerobic conditions. Main culture was inoculated with an Moo of 0.2 in 10 ml TSBYE complemented with 25 g/l sucrose and 5 mM $KNO_3$ in 15 ml Falcon Tubes at 37° C. without shaking for 48 h. Lactate was measured in the supernatant with HPLC-UV.

| | % Lactate production |
| --- | --- |
| *Bacillus toyonensis* | 100.00 |
| DSM 32540 | 147.47 |

Strain *B. subtilis* DSM 32540 produces almost 50% more lactate compared to probiotic strain of *Bacillus toyonensis*.

REFERENCES

A Halasz (2009) Book: Food quality and standards Volume III; EOLSS Publishers Co Ltd. Chapter: Lactic acid bacteria.

TA Oelschlager (2010) Mechanisms of probiotic actions—A review. International Journal of Medical Microbiology Volume 300, Issue 1, January 2010, Pages 57-62.

R Fuller 1992 Publisher: Springer science and business media Dordrecht Book: Probiotics: The scientific basis Chapter 9.8 Antimicrobial activity.

Example 8. Comparison of Performance of Swine Reared in China Fed the Novel *Bacillus subtilis* Strain DSM 32540

The experiment comprises 168 25-day weaned piglets (Landrace×Yorkshire), randomly allocated to three treatments (Table 8.1), with 8 replicates, 7 piglets with average 6.5±0.5 kg for each replicate. Three treatments were mainly based on corn-soybean meal (Table 8.2) and included; 1. Basal control (Control), 2. Control+30 g of Virginiamycin/MT of feed (AGP), 3. Control+*Bacillus subtilis* strain DSM 32540 at 250 g/MT containing $2.0*10^9$ cfu/g (DSM 32540). Experimental treatments were fed ad libitum in mash form from 1-42 days of age.

TABLE 8.1

Experimental Treatments

| Treat | Diet type | Additive Inclusion Level |
| --- | --- | --- |
| 1 | Control diet (without AGP) | — |
| 2 | Control diet + antibiotic (AGP, virginamycin (0.04 kg/t)) | — |
| 3 | Control diet + DSM 32540 | 500 g/t |

TABLE 8.2

Ingredient and nutrient composition of basal diet.

| | wt.-% |
| --- | --- |
| Ingredients | |
| Corn | 48 |
| SBM, 46% | 11.68 |
| Barley | 10 |
| Fermented SBM, 50% | 6 |
| Whey, 3.5% | 5.3 |
| Full fat Soya | 4 |
| Soya oil | 3 |
| Fish meal | 3 |
| Glucose | 2.5 |
| Cane Sugar | 2.5 |
| IS, 38% | 0.98 |
| CPM, 23% | 0.45 |
| Lys, 98% | 0.45 |
| Acidifier | 0.3 |
| Thr | 0.25 |
| Salt | 0.24 |
| Metamino | 0.2 |
| Valine | 0.08 |
| Try | 0.07 |
| Prexim | 1 |
| Nutrient composition | |
| Crude protein | 22.00 |
| Crude fiber | 3.89 |
| ME, MJ/kg | 14.23 |
| ME, kcal/kg | 3402 |
| NE, MJ/kg | 10.40 |
| NE, kcal/kg | 2485 |
| Ca (%) | 0.80 |
| Av P (%) | 0.40 |
| SID Lys | 1.35 |
| SID Met | 0.57 |

TABLE 8.2-continued

Ingredient and nutrient composition of basal diet.

| | wt.-% |
|---|---|
| SID Cys | 0.24 |
| SID M + C | 0.81 |
| SID Thr | 0.85 |
| SID Trp | 0.30 |
| SID Arg | 0.97 |
| SID Ile | 0.74 |
| SID Leu | 1.45 |
| SID Val | 0.92 |

The results of the treatments on body weight gain, feed conversion ratio, feed intake and diarrhea of the piglets are reported in Tables 3 and 4.

TABLE 8.3

Performance data from 1 to 42 d post-weaning.

| | Treatments | | |
|---|---|---|---|
| Age | Negative | Positive | DSM 32540 |
| ADG 1-42 | 0.460 | 0.482 | 0.476 |
| Av. Daily Feed intake, kg | 0.770 | 0.772 | 0.773 |
| FCR 1-42 | 2.42 | 2.34 | 2.11 |

TABLE 8.4

Diarrhea score in percent of piglets suffering diarrhea

| Treatment | Negative control | Positive control | DSM 32540 |
|---|---|---|---|
| 1~7 d | 8.99 | 7.72 | 7.72 |
| 8~21 d | 6.16 | 4.69 | 4.43 |
| 22~42 d | 2.05 | 1.73 | 1.95 |

Average daily weight gain, feed conversion ratio, feed intake as well as the diarrhea score were significantly improved by addition of the *B. subtilis* strain DSM 32540 in comparison to the negative control but similar to positive control containing AGP.

Example 9. Comparison of Performance of Swine Reared in Spain Fed the Novel *Bacillus subtilis* DSM 32540

The experiment comprises 64 21-day post-weaned piglets with an average body weight of 7.3±0.35 kg randomly allocated to 2 treatments (Table 9.1), with 6 replicates, 4 piglets for each replicate. Three treatments were mainly based on corn-soybean meal (Table 9.2) and included; 1. Basal control (Control), 2. Control+*Bacillus subtilis* strain DSM 32540 at 250 g/MT containing $2.0*10^9$ cfu/g (DSM 32540). Experimental treatments were fed ad libitum in mash form from 1-42 days of age post-weaning.

TABLE 9.1

Ingredient and nutrient composition of basal diet.

| | wt.-% |
|---|---|
| Ingredient | |
| Corn | 34.63 |
| Soybean meal, 44% CP | 26.10 |
| Barley | 10.00 |
| Whey powder | 9.00 |
| Soybean meal, full fat | 8.40 |
| Rapeseed meal | 5.00 |
| Soybean oil | 3.00 |
| Monocalciumphosphate | 1.09 |
| Limestone (CaCO$_3$) | 0.95 |
| Premix Swine | 0.50 |
| L-Lys HCl (78%) | 0.42 |
| Salt (NaCl) | 0.38 |
| MetAMINO ® | 0.24 |
| ThreAMINO ® | 0.15 |
| ValAMINO ® | 0.06 |
| TrpAMINO ® | 0.07 |
| Total | 100.0000 |
| Nutrient composition | |
| Crude protein | 22.00 |
| Crude fiber | 3.89 |
| ME, MJ/kg | 14.23 |
| ME, kcal/kg | 3402 |
| NE, MJ/kg | 10.40 |
| NE, kcal/kg | 2485 |
| Ca (%) | 0.80 |
| Av P (%) | 0.40 |
| SID Lys | 1.35 |
| SID Met | 0.57 |
| SID Cys | 0.24 |
| SID M + C | 0.81 |
| SID Thr | 0.85 |
| SID Trp | 0.30 |
| SID Arg | 0.97 |
| SID Ile | 0.74 |
| SID Leu | 1.45 |

TABLE 9.2

Animal performance between days 0 and 42, with and without diet supplementation with *B. subtilis* DSM 32540 based feed additive or antibiotic growth promoter.

| | Treatments | |
|---|---|---|
| Age | Negative | DSM 32540 |
| ADG, kg | 0.263 | 0.297 |
| Av. Daily Feed intake, kg | 0.389 | 0.429 |
| FCR | 1.507 | 1.473 |

*B. subtilis* strain DSM 32540 significantly improved all tested parameters in comparison to the negative control.

The invention claimed is:

1. A feed or foodstuff comprising:

a) *Bacillus subtilis* DSM 32540;

b) at least one ingredient selected from the group consisting of: proteins, carbohydrates, fats, additional probiotics, prebiotics, enzymes, vitamins, immune modulators, milk replacers, minerals, amino acids, coccidiostats, acid-based products, medicines, and combinations thereof; and c) at least one added carrier to improve one or more characteristics selected from the group consisting of: recovery; efficacy; physical properties; packaging and administration;

wherein:

i) when the feed or foodstuff is fed to an animal, the growth of pathogenic bacteria is reduced compared to growth in the feed or foodstuff without said *Bacillus subtilis* DSM 32540; and wherein said pathogenic bacteria are selected from the group consisting of:

*Clostridium perfringens, Clostridium difficile, Enterococcus cecorum, Streptococcus* gallinaceus and *Streptococcus suis* bacteria; and ii) said *Bacillus subtilis* DSM 32540 is able to grow in the presence of 2 mM bile.

2. The feed or foodstuff of claim 1, wherein said feed or foodstuff is a dry product and the added carrier is selected from the group consisting of: anti-caking agents; anti-oxidation agents; bulking agents; and protectants.

3. The feed or foodstuff of claim 1, wherein the *Bacillus subtilis* DSM 32540 is in the feed or foodstuff in an amount sufficient to reduce *Clostridium perfringens* growth in an animal gut by at least 0.5 log.

4. The feed or foodstuff of claim 3, wherein the *Bacillus subtilis* strain is present at $1 \times 10^3$ to $2 \times 10^{12}$ colony forming units (CFU) per gram of feed or foodstuff.

5. A feed or foodstuff comprising a naturally non-occurring mutant of *Bacillus subtilis* DSM 32540, wherein said mutant is not found in nature and comprises a DNA sequence identity to DSM 32540 of at least 99.5%;

wherein:

i) said mutant of *Bacillus subtilis* DSM 32540 inhibits the growth of at least one of: *Clostridium perfringens, Clostridium difficile, Enterococcus cecorum, Streptococcus* gallinaceus and *Streptococcus suis* bacteria;

ii) said mutant of *Bacillus subtilis* DSM 32540 is able to grow in the presence of 2 mM bile; and iii) the feed or foodstuff further comprises at least one ingredient selected from the group consisting of: proteins, carbohydrates, fats, additional probiotics, prebiotics, enzymes, vitamins, immune modulators, milk replacers, minerals, amino acids, coccidiostats, acid-based products, medicines, and combinations thereof and an added carrier selected from the group consisting of: anti-caking agents; anti-oxidation agents; bulking agents; and protectants;

wherein the mutant of *Bacillus subtilis* DSM 32540 is present in said feed or foodstuff in an amount sufficient to reduce pathogenic bacterial growth in an animal gut by at least 0.5 log compared to the same feed or foodstuff in the absence of the mutant of *Bacillus subtilis* DSM 32540.

6. The feed or foodstuff of claim 5, wherein said feed or foodstuff is a dry product and further comprises one or more carriers selected from the group consisting of: anti-caking agents; anti-oxidation agents; bulking agents; and protectants.

7. The feed or foodstuff of claim 5, wherein said feed or foodstuff inhibits or decreases the growth of *Clostridium perfringens* in said animal.

8. The feed or foodstuff of claim 7, wherein the mutant of *Bacillus subtilis* DSM 32540 is present at $1 \times 10^3$ to $2 \times 10^{12}$ CFU per gram of feed or foodstuff.

9. The feed or foodstuff of claim 5, wherein said mutant of *Bacillus subtilis* DSM 32540 exhibits a *Clostridium perfringens* strain ATCC 13124b1945, *Streptococcus* gallinaceus strain DSM 15349 and/or *Streptococcus suis* strain DSM 9682 clearance of at least 10 mm in a well diffusion antagonism assay on agar plates prepared with LB medium that is supplemented with trace elements of DSMZ media 1032.

10. The feed or foodstuff of claim 5, wherein the mutant of *Bacillus subtilis* DSM 32540 is present in the feed or foodstuff in an amount sufficient to reduce the growth of *Clostridium perfringens, Clostridium difficile, Enterococcus cecorum, Streptococcus* gallinaceus and *Streptococcus suis* bacteria by at least 1 log in infected animals administered a diet of the feed or foodstuff on a daily basis or to reduce the mortality of infected animals by at least 2% compared to animals administered the same diet but where the feed or foodstuff does not comprise the *Bacillus subtilis* mutant.

11. The feed or foodstuff of claim 5, wherein said mutant of *B. subtilis* DSM 32540 is a genetically engineered bacteria or said mutant has a mutation resulting from growing bacteria in the presence of a mutagen.

12. A feed or foodstuff comprising fermentation products that comprise *B. subtilis* DSM 32540 and wherein, when the feed or foodstuff is fed to an animal, it inhibits the growth of at least one of: *Clostridium perfringens, Clostridium difficile, Enterococcus* cecorum, *Streptococcus* gallinaceus and *Streptococcus suis* bacteria compared to growth when the feed or foodstuff is without said *Bacillus subtilis* DSM 32540; and wherein the *Bacillus subtilis* DSM 32540 is present in the feed or foodstuff in an amount sufficient to reduce pathogenic bacterial growth in an animal gut by at least 0.5 log when fed to said animal.

13. The feed or foodstuff of claim 12, further comprising one or more carriers selected from the group consisting of: anti-caking agents; anti-oxidation agents; and bulking agents.

14. The feed or foodstuff of claim 12, wherein the *Bacillus subtilis* strain is present at $1 \times 10^3$ to $2 \times 10^{12}$ CFU per gram of composition.

15. The feed or foodstuff of claim 13, wherein the added carrier is an anti-caking agent or a bulking agent and the composition is a dry product.

\* \* \* \* \*